US011992612B2

(12) United States Patent
Wada et al.

(10) Patent No.: US 11,992,612 B2
(45) Date of Patent: May 28, 2024

(54) CONTINUOUS POSITIVE AIRWAY PRESSURE (CPAP) DEVICE

(71) Applicant: Murata Manufacturing Co., Ltd., Kyoto (JP)

(72) Inventors: Hiroaki Wada, Nagaokakyo (JP); Yuzo Higashiyama, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 909 days.

(21) Appl. No.: 17/035,898

(22) Filed: Sep. 29, 2020

(65) Prior Publication Data
US 2021/0008310 A1     Jan. 14, 2021

Related U.S. Application Data

(63) Continuation of application No. PCT/JP2019/012777, filed on Mar. 26, 2019.

(30) Foreign Application Priority Data

Mar. 30, 2018   (JP) ................................ 2018-067068

(51) Int. Cl.
*A61M 16/00*     (2006.01)
*A61M 16/10*     (2006.01)

(52) U.S. Cl.
CPC ....... *A61M 16/0066* (2013.01); *A61M 16/106* (2014.02); *A61M 2205/10* (2013.01);
(Continued)

(58) Field of Classification Search
CPC ............ A61M 16/0066; A61M 16/106; A61M 2205/3334; A61M 2205/42; F04D 29/44
See application file for complete search history.

(56) References Cited

U.S. PATENT DOCUMENTS

2011/0226245 A1   9/2011   Gillespie
2012/0199129 A1   8/2012   Kenyon et al.
(Continued)

FOREIGN PATENT DOCUMENTS

EP     3128184 A1    2/2017
JP     H05-073296 U    10/1993
(Continued)

OTHER PUBLICATIONS

International Search Report for International Application No. PCT/JP2019/012777 dated Jun. 11, 2019.
(Continued)

*Primary Examiner* — Margaret M Luarca
(74) *Attorney, Agent, or Firm* — Pearne & Gordon LLP

(57) ABSTRACT

A CPAP device includes a housing. A suction port is provided in a top plate portion of a casing of the air blower. The air blower chamber has a facing wall portion facing the top plate portion with a distance therebetween. A wall portion defining the air blower chamber is provided with an introduction port for introducing external air. In a space between the facing wall portion and the top plate portion, a flow adjustment portion that partitions the space into flow paths arranged side by side around a rotation axis is provided. An outer end portion and an inner end portion of each of the flow paths in a direction orthogonal to the rotation axis are respectively constituted of a first open end and a second open end, the first open end and the second open end being open along the direction orthogonal to the rotation axis.

14 Claims, 13 Drawing Sheets

(52) U.S. Cl.
CPC ............ *A61M 2205/3331* (2013.01); *A61M 2205/3334* (2013.01); *A61M 2205/42* (2013.01); *A61M 2205/52* (2013.01)

(56) References Cited

U.S. PATENT DOCUMENTS

2014/0069432 A1  3/2014  Mebasser et al.
2016/0184539 A1  6/2016  Suzuki et al.

FOREIGN PATENT DOCUMENTS

| JP | H11-117899 A | 4/1999 |
| JP | 2011-502019 A | 1/2011 |
| JP | 2014-512479 A | 5/2014 |
| JP | 2015-033522 A | 2/2015 |
| JP | 2016-020658 A | 2/2016 |
| WO | 2015/151653 A1 | 10/2015 |

OTHER PUBLICATIONS

Written Opinion for International Application No. PCT/JP2019/012777 dated Jun. 11, 2019.

CONTINUOUS POSITIVE AIRWAY PRESSURE (CPAP) DEVICE

CROSS REFERENCE TO RELATED APPLICATION

This is a continuation of International Application No. PCT/JP2019/012777 filed on Mar. 26, 2019 which claims priority from Japanese Patent Application No. 2018-067068 filed on Mar. 30, 2018. The contents of these applications are incorporated herein by reference in their entireties.

TECHNICAL FIELD

The present disclosure relates to a CPAP (Continuous Positive Airway Pressure) device that sends air, which is suctioned into the device, into a user's airway in order to treat sleep apnea syndrome.

BACKGROUND ART

A cause of sleep apnea syndrome involving pauses in breathing during sleep is a physically narrowed airway. An airway is a path via which air flows. An exemplary effective treatment method for the sleep apnea syndrome is a treatment method using a CPAP device.

The CPAP device is a device that continuously sends air to the airway to open the airway in order to prevent apnea during sleep. More specifically, the CPAP device includes an air blower and sends air, which is suctioned into the device, to a mask attached to the nose or mouth of a user via an air tube.

Japanese Patent Laying-Open No. 2015-33522 (PTL 1) specifically discloses a configuration of such a CPAP device, for example. In the CPAP device disclosed in this patent publication, an air blower including a casing having an impeller accommodated therein is accommodated inside a housing of the CPAP device, and an air inlet port provided in an outer surface of the housing and an suction port provided in the casing of the air blower are connected to each other through a duct-like suction flow path.

BRIEF SUMMARY

Here, since the CPAP device is used when the user goes to bed and while the user sleeps, quietness is required during an operation of the CPAP device. Quietness during the operation is hindered mainly by factors such as operation sounds of a drive motor and a wind noise, which are generated when the air blower is operated. By suppressing the leakage of these noises to outside of the device, quietness can be improved.

Regarding this point, in the CPAP device disclosed in the above patent publication, the duct-like suction flow path is constituted of noise reduction materials, and the suction flow path is routed in a meandering manner, with the result that a noise generated in the air blower is suppressed from leaking to the outside of the device.

In addition to the above-described operational quietness, there is a strong demand for downsizing of the CPAP device. This is due to the following reason: since the CPAP device is required to be continuously used every day, the user needs to carry the CPAP device with him/her when the user stays out overnight, for example.

Regarding this point, in the CPAP device disclosed in the above patent publication PTL 1, since the duct-like suction flow path is substantially orthogonally connected to an opening plane of the suction port provided in the casing of the air blower, it is necessary to secure a large space for a portion adjacent to the suction port, which results in a large thickness of the device. Accordingly, the device cannot be sufficiently downsized (particularly, the device cannot be sufficiently thinned).

Here, if the air inlet port of the housing is disposed at a location close to the suction port in order to reduce the space of the portion adjacent to the suction port, a noise immediately leaks to the outside of the device, thus making it difficult to ensure the above-described quietness during its operation.

On the other hand, if the suction flow path at a portion connected to the suction port is bent at a substantially right angle in order to reduce the space of the portion adjacent to the suction port, a high flow path resistance is caused at that portion to increase pressure loss, with the result that the air sending performance of the air blower is significantly decreased. When the rotation speed of the air blower is increased or the size of the air blower is increased in order to compensate for the decreased air sending performance, noise and power consumption are increased and the size of the device is increased, which would be disadvantageous.

Thus, the downsizing of the device and the quietness are in a trade-off relation. Improvement in this point has been strongly requested.

Thus, the present disclosure has been made to solve the above-described problem and has an object to provide a downsized CPAP device that can ensure quietness during its operation.

A CPAP device according to the present disclosure sends air suctioned into the CPAP device to an airway of a user, and includes: an air blower; and a housing in which an air blower chamber is provided to accommodate the air blower. The air blower includes an impeller rotatable about a rotation axis, a drive unit that drives to rotate the impeller, and a casing surrounding the impeller. The casing is provided with a suction port for suctioning air inside the air blower chamber into the casing, and a discharge port for discharging air inside the casing to outside of the casing. The suction port is located at a portion of a top plate portion overlapping with the rotation axis, the top plate portion being one of a pair of wall portions of the casing, the pair of wall portions sandwiching the impeller in a direction in which the rotation axis extends. Wall portions defining the air blower chamber include a wall portion that is located at a portion not overlapping with the top plate portion when seen along the direction in which the rotation axis extends and that is provided with an introduction port for introducing air outside the housing into the air blower chamber. The air blower chamber has a facing wall portion facing the top plate portion with a distance between the facing wall portion and the top plate portion. In a space between the facing wall portion and the top plate portion, a flow adjustment portion that partitions at least a portion of the space into a plurality of flow paths arranged side by side around the rotation axis is provided. An outer end portion and an inner end portion of each of the plurality of flow paths in a direction orthogonal to the rotation axis are respectively constituted of a first open end and a second open end, the first open end and the second open end being open along the direction orthogonal to the rotation axis.

Preferably in the CPAP device according to the present disclosure, an opening area of a first open end of a flow path of the plurality of flow paths on the introduction port side when seen from the suction port is smaller than an opening area of a first open end of a flow path of the plurality of flow paths on a side opposite to the introduction port side when seen from the suction port.

Preferably in the CPAP device according to the present disclosure, a first open end provided in a flow path of the plurality of flow paths at a shorter distance from the introduction port has a smaller opening area.

In the CPAP device according to the present disclosure, the flow adjustment portion may include a plurality of flow adjustment plates that extend radially with respect to the rotation axis.

In the CPAP device according to the present disclosure, an inner end portion of each of the plurality of flow adjustment plates may reach an edge of the suction port.

In the CPAP device according to the present disclosure, the plurality of flow adjustment plates may include main flow adjustment plates each having a relatively long length and additional flow adjustment plates each having a relatively short length. In that case, one or a plurality of the additional flow adjustment plates are preferably disposed between adjacent main flow adjustment plates.

Preferably in the CPAP device according to the present disclosure, the flow adjustment portion further includes an auxiliary flow adjustment plate in a form of a plate, the auxiliary flow adjustment plate being located on the facing wall portion side of each of the plurality of flow adjustment plates, the auxiliary flow adjustment plate closing each of the plurality of flow paths at a location on the facing wall portion side.

In the CPAP device according to the present disclosure, the flow adjustment portion may be provided on the top plate portion to protrude toward the facing wall portion.

In the CPAP device according to the present disclosure, the flow adjustment portion may be provided on the facing wall portion to protrude toward the top plate portion.

According to the present disclosure, there can be provided a downsized CPAP device that can ensure quietness.

DETAILED DESCRIPTION OF EMBODIMENTS

Figure 1:
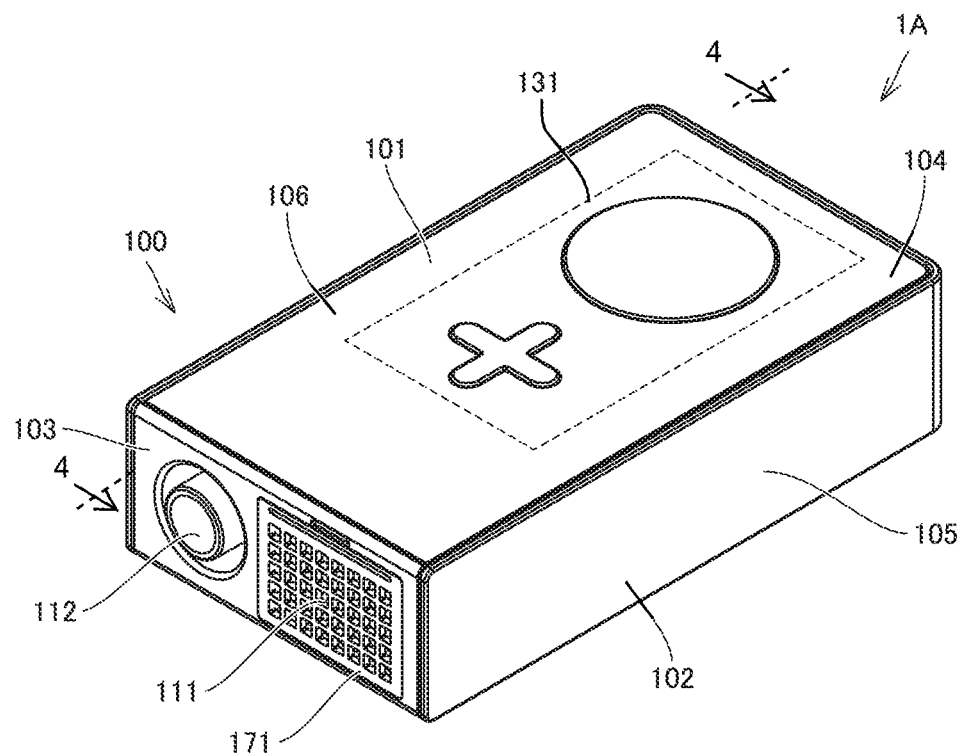
FIG. 1 is an example of a perspective view of a CPAP device according to a first embodiment.

Hereinafter, embodiments of the present disclosure will be described in detail with reference to figures. It should be noted that in the below-described embodiments, the same or corresponding portions are denoted by the same reference characters in the figures and are not described repeatedly.

1. The First Embodiment

FIG. 1 is a perspective view of a CPAP device according to a first embodiment of the present disclosure. First, a schematic configuration of a CPAP device 1A according to the present embodiment will be described with reference to FIG. 1.

As shown in FIG. 1, CPAP device 1A has a flat, substantially rectangular parallelepiped outer shape, and has an outer shell constituted of a housing 100. Housing 100 has: a top plate 101 and a bottom plate 102, which are to be located side by side in the vertical direction in a state of use; and four side plates, i.e., the first to fourth side plates 103 to 106 that each connect top plate 101 to bottom plate 102.

Top plate 101 of housing 100 is provided with a manipulation unit 131. On the other hand, bottom plate 102 of housing 100 constitutes a placement surface to be placed on a floor surface, a table, or the like in the state of use. Among the four side plates of housing 100, first side plate 103 is provided with: an air inlet port 111 for suctioning air from the outside of housing 100 into the inside of housing 100; and an air outlet port 112 for discharging air from the inside of housing 100 to the outside of housing 100.

Figure 4:
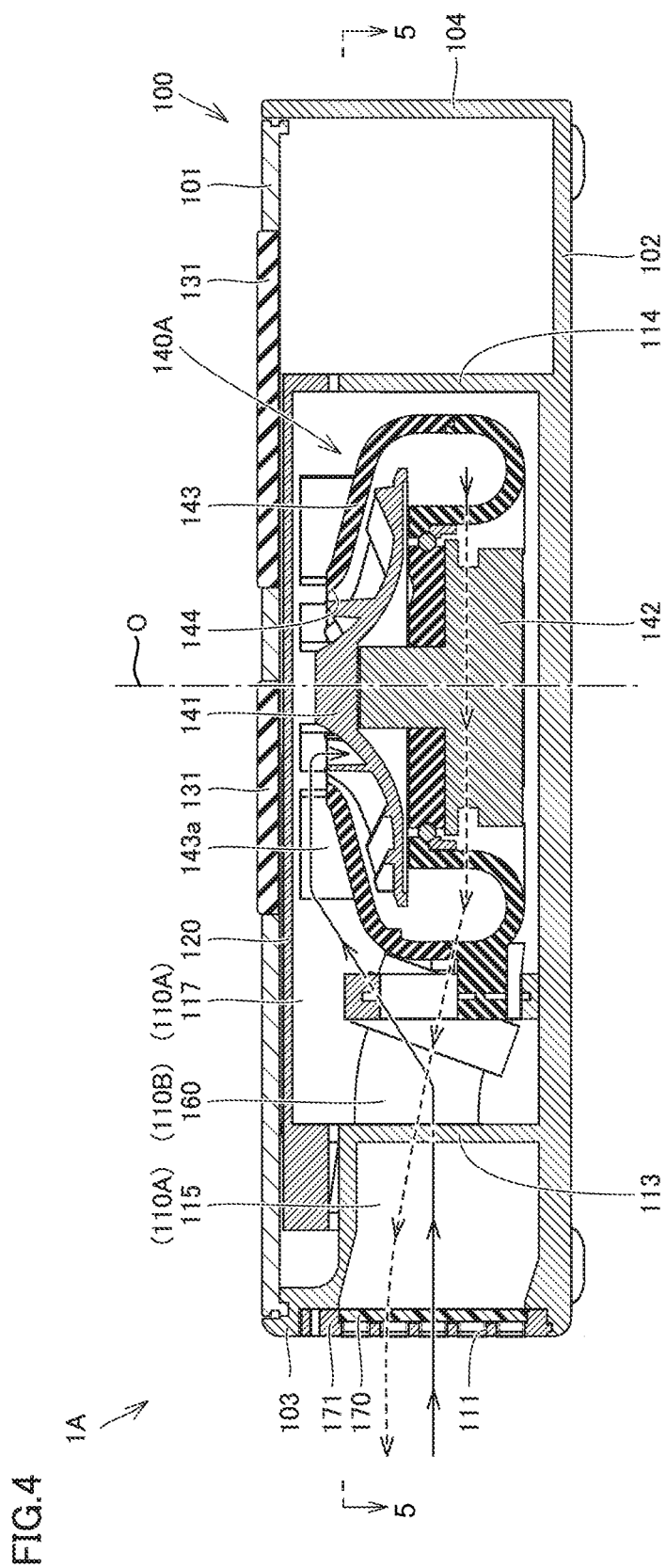
FIG. 4 is an example of a schematic cross sectional view of the CPAP device shown in FIG. 1.
Figure 5:
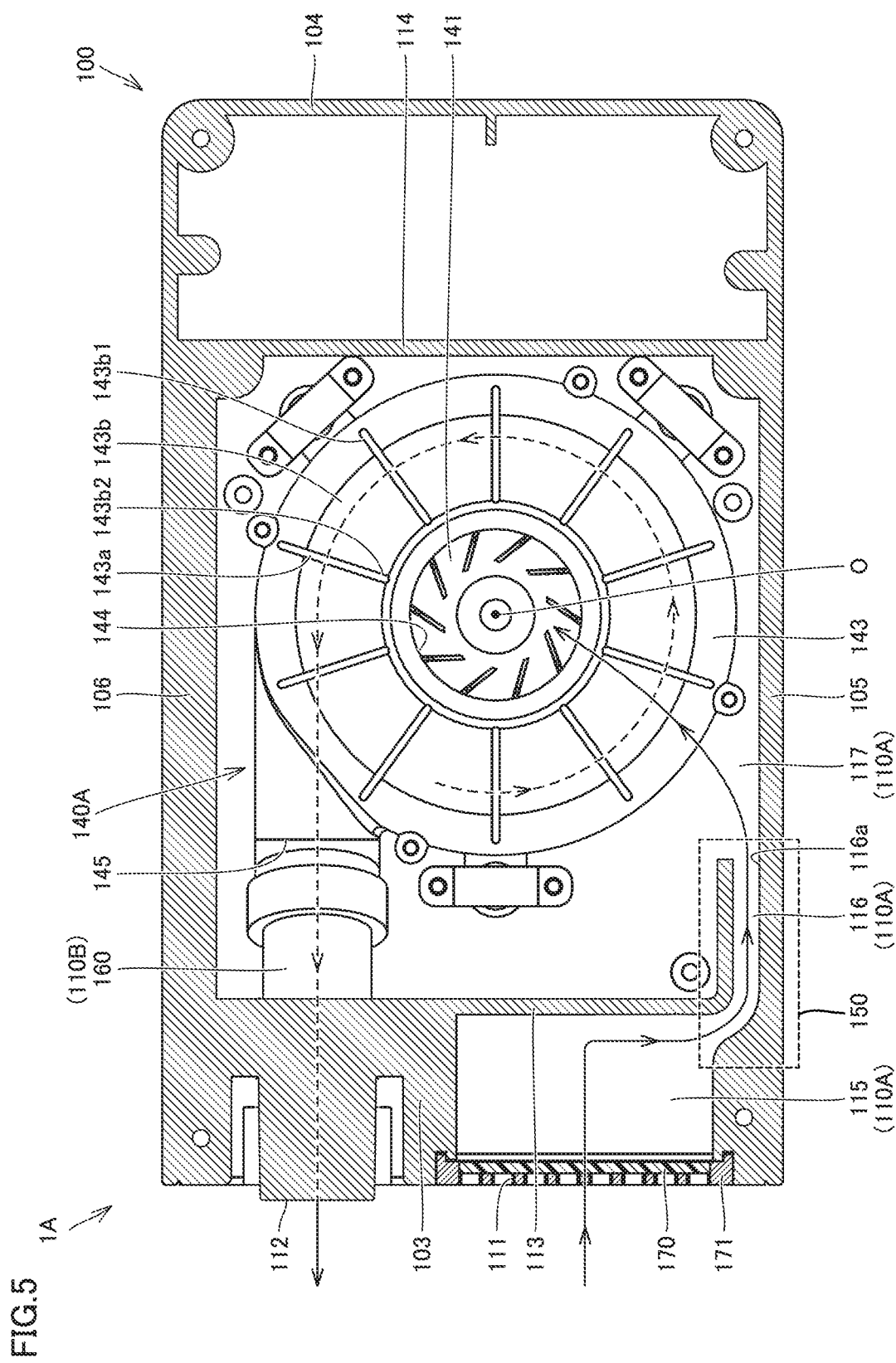
FIG. 5 is an example of a schematic cross sectional view taken along a 5-5 line shown in FIG. 4.

Here, a filter 170, shown in FIGS. 4 and 5, for capturing a foreign matter such as dust in air is installed at air inlet port 111. In order to fix filter 170 to first side plate 103, a filter cover 171 constituting a portion of housing 100 is attached to first side plate 103. Filter cover 171 is provided with a plurality of hole portions in the form of a matrix, and air inlet port 111 is constituted of the plurality of hole portions.

On the other hand, air outlet port 112 has a nozzle-like shape to allow a below-described air tube 2 to be connected to air outlet port 112.

Figure 3:
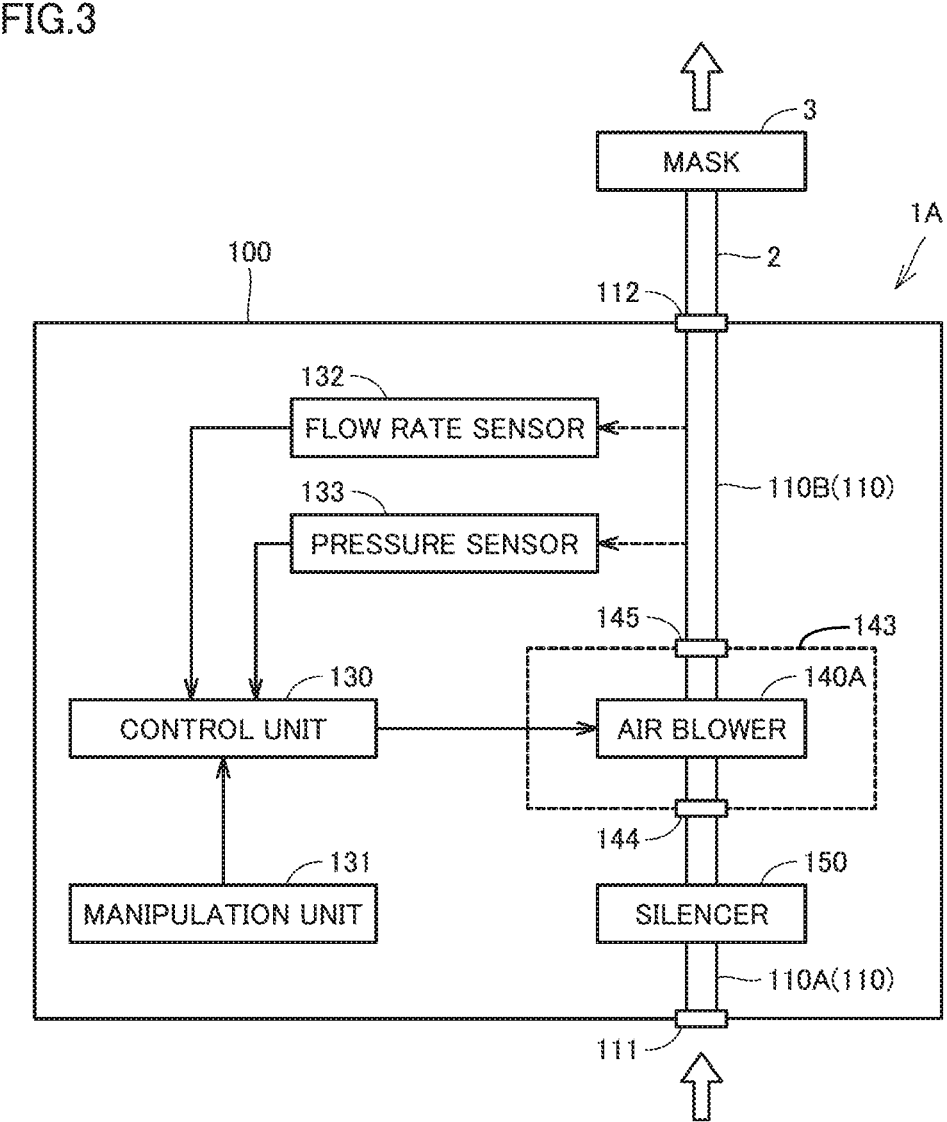
FIG. 3 is an example of a diagram showing configurations of functional blocks of the CPAP device shown in FIG. 1.

A control unit 130, a flow rate sensor 132, a pressure sensor 133, an air blower 140A, an air blower chamber 117 accommodating air blower 140A therein, a silencer 150, and the like, are provided inside housing 100, as shown in FIGS. 3 to 5. The internal structure of housing 100 will be described in detail later.

Figure 2:
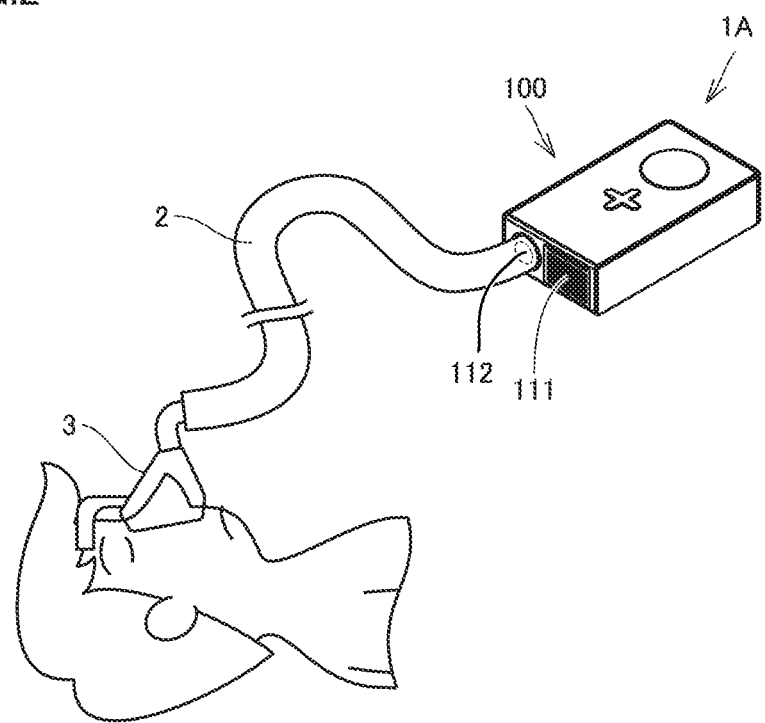
FIG. 2 is an example of a schematic view showing a state of use of the CPAP device shown in FIG. 1.

FIG. 2 is a schematic view showing a state of use of the CPAP device shown in FIG. 1. Next, the state of use of CPAP device 1A according to the present embodiment will be described with reference to FIG. 2.

As shown in FIG. 2, CPAP device 1A is used when the user goes to bed and while the user sleeps. CPAP device 1A is used in such a state that CPAP device 1A is placed beside the user on a floor surface, a table, or the like. In use, one end of air tube 2 is connected to air outlet port 112 provided in housing 100, and a mask 3 is connected to the other end of air tube 2.

Thus, in the state of use, when air blower 140A installed inside housing 100 is driven, air is suctioned from air inlet port 111 provided in housing 100 into CPAP device 1A, and the suctioned air is discharged from air outlet port 112 provided in housing 100 to the outside of CPAP device 1A. Accordingly, the air discharged from air outlet port 112 is sent to the user's airway via air tube 2 and mask 3.

Here, mask 3 is attached and is worn to cover, for example, the nose or mouth of the user. It should be noted that a suitable shape and structure of mask 3 for the user can be selected among various types of masks, and the shape and structure shown in FIG. 2 are merely examples.

It should be noted that CPAP device 1A is a device for opening the airway by continuously sending air to the airway in synchronization with breathing of the user in order to prevent apnea during sleep. Therefore, in CPAP device 1A, in the above-described state of use, various types of controls, such as a feedback control and a feedforward control are performed by below-described control unit 130 based on a flow rate value detected by flow rate sensor 132, a pressure value detected by pressure sensor 133, and the like as described later. As a result, the rotation speed of air blower 140A is increased or decreased to adjust an amount of sending air, and the user is prevented from suffering from apnea during sleep.

FIG. 3 is a diagram showing configurations of functional blocks of the CPAP device shown in FIG. 1. Next, the configurations of the functional blocks of CPAP device 1A according to the present embodiment will be described with reference to FIG. 3.

As shown in FIG. 3, CPAP device 1A includes control unit 130, manipulation unit 131, flow rate sensor 132, pressure sensor 133, air blower 140A, and silencer 150. In addition to air inlet port 111 and air outlet port 112 described above, housing 100 of CPAP device 1A is provided with an air sending path 110. Air sending path 110 is configured to connect air inlet port 111 to air outlet port 112.

Air blower 140A is provided on air sending path 110. Air blower 140A is constituted of, for example, a centrifugal fan. Air blower 140A is installed in below-described air blower chamber 117, as shown in, e.g., FIGS. 4 and 5) provided in housing 100, and is therefore disposed on air sending path 110.

Here, air blower 140A has a casing 143 and casing 143 is provided with a suction port 144 and a discharge port 145 of air blower 140A. Therefore, air sending path 110 includes: an upstream side flow path portion 110A that connects air inlet port 111 provided in housing 100 to suction port 144 provided in air blower 140A; and a downstream side flow path portion 110B that connects discharge port 145 provided in air blower 140A to air outlet port 112 provided in housing 100.

Silencer 150 is provided at upstream side flow path portion 110A, which is a portion of air sending path 110 located between air inlet port 111 and suction port 144. Silencer 150 serves to suppress a noise (an operation sound of a below-described drive motor 142, as shown in FIG. 4, provided in air blower 140A, a wind noise, or the like) generated in air blower 140A from leaking to the outside via air inlet port 111. Details thereof will be described later.

Control unit 130 includes, as main components, a CPU (Central Processing Unit) that executes a program, a ROM (Read Only Memory)/RAM (Random Access Memory), a drive circuit that operates air blower 140A, and the like. The ROM/RAM includes: a ROM for storing data in a non-volatile manner; and a RAM for storing, in a volatile manner, data generated by the CPU executing a program or data input via manipulation unit 131. The components of control unit 130 are connected to each other through a data bus.

Processing by the CPU is implemented by each hardware and software executed by the CPU. Such software may be stored in advance in the ROM/RAM. Reception of a manipulation on manipulation unit 131, control of drive motor 142 for driving air blower 140A, and the like are also implemented by software.

Control unit 130 is supplied with power from an internal power supply (not shown) or an external power supply (not shown). For connection to the external power supply, an AC (Alternating Current) adapter (not shown) or the like is used, for example. As with control unit 130, power is supplied to flow rate sensor 132 and pressure sensor 133 by an internal power supply (not shown) or an external power supply (not shown). Flow rate sensor 132 is a sensor for measuring a flow rate of air between CPAP device 1A and air tube 2, and pressure sensor 133 is a sensor for measuring a pressure of air sent by air blower 140A. Although not described in detail here, the rotation speed of air blower 140A is increased or decreased by control unit 130 performing control such as feedback control or feedforward control based on the flow rate value detected by flow rate sensor 132, the pressure value detected by pressure sensor 133, and the like.

It should be noted that CPAP device 1A may be additionally provided with a display unit constituted of an LCD (Liquid Crystal Display), an organic EL (Electro-Luminescence) display, or the like. Manipulation unit 131 does not need to be a button having a physical shape as shown in the figure, and may be, for example, a touch panel or the like provided on a display surface of the LCD.

Figure 6:
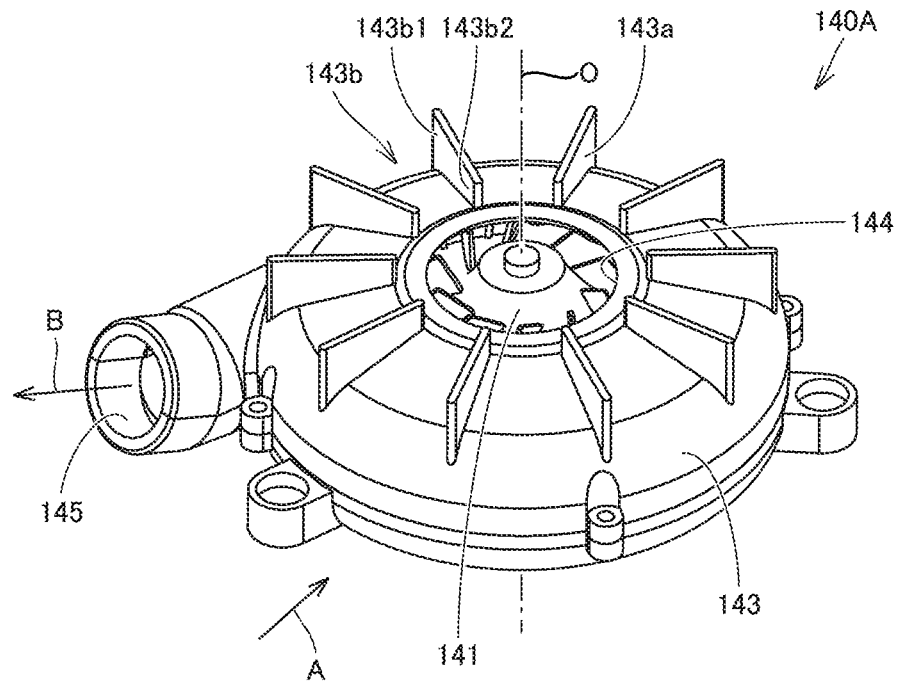
FIG. 6 is an example of a perspective view of an air blower shown in FIGS. 4 and 5.

FIG. 4 is a schematic cross sectional view of the CPAP device shown in FIG. 1, and FIG. 5 is a schematic cross sectional view taken along a 5-5 line shown in FIG. 4. FIG. 6 is a perspective view of the air blower shown in FIGS. 4 and 5. Next, an internal structure of CPAP device 1A according to the present embodiment and a flow of air in CPAP device 1A in the state of use will be described with reference to FIGS. 4 to 6. It should be noted that in each of FIGS. 4 and 5, the flow of air caused by an operation of air blower 140A is schematically indicated by arrows.

As shown in FIGS. 4 and 5, a space inside housing 100 is divided into a plurality of chambers by providing various types of wall portions, hoses, and the like. The plurality of chambers include an expanded portion 115, a narrowed portion 116, and an air blower chamber 117. Expanded portion 115, narrowed portion 116, and air blower chamber 117 correspond to upstream side flow path portion 110A described above.

Expanded portion 115 is provided adjacent to air inlet port 111 provided in first side plate 103 of housing 100. The cross sectional area of expanded portion 115 orthogonal to the flow direction of air (i.e., the area of expanded portion 115 in a cross section parallel to the opening plane of air inlet port 111) is relatively large to reduce pressure loss that can occur in air inlet port 111. It should be noted that the cross sectional area of expanded portion 115 being orthogonal to the flow direction of air is larger than the cross sectional area of below-described narrowed portion 116 being orthogonal to the flow direction of air. As described above, air inlet port 111 is constituted of the plurality of hole portions arranged in the form of a matrix in filter cover 171.

Narrowed portion 116 is provided adjacent to expanded portion 115. Narrowed portion 116 is formed by providing a separation wall 113 inside housing 100, and the cross sectional area of narrowed portion 116 being orthogonal to the flow direction of air (i.e., the area of narrowed portion 116 in the cross section being parallel to the opening plane of air inlet port 111) is relatively smaller than that of expanded portion 115 described above. It should be noted that the cross sectional area of narrowed portion 116 being orthogonal to the flow direction of air is smaller than the cross sectional area of expanded portion 115 being orthogonal to the flow direction of air. An end portion of narrowed portion 116 on the air blower chamber 117 side functions as an introduction port 116a for introducing air into air blower chamber 117.

Air blower chamber 117 is provided adjacent to narrowed portion 116, and air blower 140A is accommodated therein. Air blower chamber 117 is constituted of a space having a flat, substantially rectangular parallelepiped shape mainly defined by: separation wall 113 and a partition wall 114 provided inside housing 100; an upper cover 120 disposed inside housing 100 and close to top plate 101 of housing 100; and bottom plate 102, third side plate 105, and fourth side plate 106 of housing 100. The cross sectional area of air blower chamber 117 being orthogonal to the flow direction of air (i.e., the area of air blower chamber 117 in the cross section parallel to the opening plane of air inlet port 111) is relatively large. Air blower chamber 117 is constituted of a relatively large space that occupies a large part of housing 100. It should be noted that the cross sectional area of air blower chamber 117 orthogonal to the flow direction of air is larger than the cross sectional area of narrowed portion 116 orthogonal to the flow direction of air.

Here, air sending path 110 at the portion corresponding to expanded portion 115 and narrowed portion 116 is a region in which the cross sectional area thereof orthogonal to the flow direction of air is abruptly increased from the downstream side toward the upstream side in the flow direction of air. This region functions as silencer 150 described above.

In other words, silencer 150 is configured as a so-called muffler type silencer constituted of expanded portion 115 and narrowed portion 116 disposed side by side in the extending direction of air sending path 110. The cross sectional area of narrowed portion 116 being orthogonal to the flow direction of air is smaller than the cross sectional area of expanded portion 115 being orthogonal to the flow direction of air as described above. Narrowed portion 116 is disposed on the downstream side relative to expanded portion 115 along the flow direction of air. With such a configuration, a noise generated in air blower 140A is attenuated by irregular reflection or the like when passing through silencer 150, with the result that leakage of noise through air inlet port 111 can be suppressed.

It should be noted that the cross sectional area of narrowed portion 116 being orthogonal to the flow direction of air is preferably less than or equal to ½ of the cross sectional area of expanded portion 115 being orthogonal to the flow direction of air. With such a configuration, the leakage of noise through air inlet port 111 can be effectively suppressed.

Silencer 150 having the above configuration is effective in reducing a noise in a relatively high frequency band of approximately 1500 Hz or more, but is not necessarily capable of sufficiently reducing a noise in a lower frequency band. However, the occupied volume of silencer 150 having the above configuration can be sufficiently small in housing 100, thus contributing to downsizing of CPAP device 1A.

Therefore, when it is particularly required to reduce not only noises in the relatively high frequency bands but also noises in the lower frequency bands, noises can be reduced in wider frequency bands by, for example, further attaching a sound absorbing material to the inner wall surface of housing 100 constituting upstream side flow path portion 110A, while achieving the downsizing of CPAP device 1A.

As described above, air blower 140A includes, for example, a centrifugal fan, and is fixed to bottom plate 102 of housing 100 with air blower 140A being accommodated in air blower chamber 117. Air blower 140A includes an impeller 141, drive motor 142 serving as a drive unit, and casing 143.

Impeller 141 includes a so-called turbo fan, has a shaft portion at its center, and has a blade portion extending from the shaft portion toward outside. Impeller 141 is rotatable about a rotation axis O defined by the shaft portion.

The shaft portion of impeller 141 is fixed to an output shaft of drive motor 142, and impeller 141 is therefore rotated about rotation axis O by driving of drive motor 142. The rotation of impeller 141 causes stirring of air to apply centrifugal force to the air, with the result that an airflow is generated inside casing 143 to suction air from suction port 144 provided in casing 143 and discharge air from discharge port 145 provided in casing 143.

Here, suction port 144 of air blower 140A is provided in casing 143 at a position above the shaft portion of impeller 141. A wall portion of casing 143 provided with suction port 144 is a region corresponding to a top plate portion of a pair of wall portions of casing 143 sandwiching impeller 141 in a direction in which rotation axis O extends. The top plate portion is located opposite to the drive motor 142 side when seen from impeller 141. It should be noted that suction port 144 is located to overlap with rotation axis O.

The top plate portion of casing 143 is located so as to face upper cover 120 defining air blower chamber 117, and so as to be separated therefrom by a predetermined distance. Accordingly, a clearance to be included in air blower chamber 117 is provided between the top plate portion of casing 143 and upper cover 120, and suction port 144 communicates with the clearance. Upper cover 120 corresponds to a facing wall portion facing the top plate portion of casing 143.

It should be noted that introduction port 116a, which is the end portion of narrowed portion 116 on the air blower chamber 117 side, is provided to be separated by a predetermined distance from suction port 144 provided in casing 143 of air blower 140A. Thus, introduction port 116a is provided in a wall portion defining air blower chamber 117 at a location not overlapping with the top plate portion of casing 143 of air blower 140A when seen along the direction in which the rotation axis O extends.

On the other hand, discharge port 145 of air blower 140A is provided in casing 143 at a position that is located in the tangential direction of the outer edge of impeller 141 when seen along the rotation axis O of impeller 141. Discharge port 145 of air blower 140A is disposed to be separated from impeller 141 by a predetermined distance. Discharge port 145 of air blower 140A is connected to the other end of a hose 160 installed to cross air blower chamber 117 and having one end connected to air outlet port 112 provided in housing 100. A space inside hose 160 corresponds to downstream side flow path portion 110B described above.

Thus, in the state of use, air suctioned from air inlet port 111 is discharged from air outlet port 112 via air sending path 110 as described above. More specifically, air suctioned from air inlet port 111 passes through expanded portion 115, narrowed portion 116, air blower chamber 117, air blower 140A, and hose 160 in housing 100 in this order, and is then discharged from air outlet port 112.

In this occasion, as shown in FIG. 6, air flowing into air blower chamber 117 via introduction port 116a flows into suction port 144 provided in casing 143 of air blower 140A in a direction substantially orthogonal to the rotation axis O of air blower 140A (i.e., the direction of arrow A shown in the FIG. 6), and is then discharged from discharge port 145 provided in casing 143 of air blower 140A in a direction substantially orthogonal to the rotation axis O of air blower 140A (i.e., the direction of arrow B shown in the FIG. 6).

Here, as shown in FIGS. 4 to 6, in CPAP device 1A according to the present embodiment, a plurality of flow adjustment plates 143a protruding toward the upper cover 120 side are provided on the top plate portion of casing 143 of air blower 140A, and a flow adjustment portion is constituted of the plurality of flow adjustment plates 143a. The flow adjustment portion with the plurality of flow adjustment plates 143a adjusts the flow of air suctioned from the outside of casing 143 of air blower 140A into casing 143 via suction port 144.

Specifically, the plurality of flow adjustment plates 143a are provided to extend radially with respect to the rotation axis O, and are therefore located to surround suction port 144. By providing the plurality of flow adjustment plates 143a, the space between the top plate portion of casing 143 of air blower 140A and upper cover 120 is partitioned into a plurality of flow paths 143b arranged side by side around the rotation axis O.

An outer end portion and an inner end portion of each of the plurality of flow paths 143b in the direction orthogonal to the rotation axis O are open along the direction orthogonal to the rotation axis O. Thus, the outer end portion is configured as a first open end 143b1, and the inner end portion is configured as a second open end 143b2.

It should be noted that in CPAP device 1A according to the present embodiment, the plurality of flow adjustment plates 143a are provided at equal intervals around the rotation axis O. Thus, first open ends 143b1 of the plurality of flow paths 143b have the same opening area, and second open ends 143b2 of the plurality of flow paths 143b also have the same opening area.

Further, in CPAP device 1A according to the present embodiment, second open ends 143b2 of the plurality of flow adjustment plates 143a are located to be outwardly separated from the outer edge of suction port 144 by a predetermined distance. Thus, flow adjustment plates 143a are not located at a portion meeting suction port 144, but are located only in the surroundings of suction port 144.

Here, each of the plurality of flow adjustment plates 143a may be disposed such that the upper end thereof (i.e., the end thereof on the upper cover 120 side) is located to be separated from upper cover 120 by a predetermined distance as shown in FIG. 4, or may be disposed such that the upper end thereof is in abutment with upper cover 120.

With such a configuration, even when upper cover 120 serving as the facing wall portion is disposed close to suction port 144 of air blower 140A, the occurrences of a large pressure loss can be suppressed in the vicinity of suction port 144. The following describes a reason thereof in detail by comparing CPAP device 1A according to the present embodiment with a CPAP device according to a comparative example.

Figure 7:
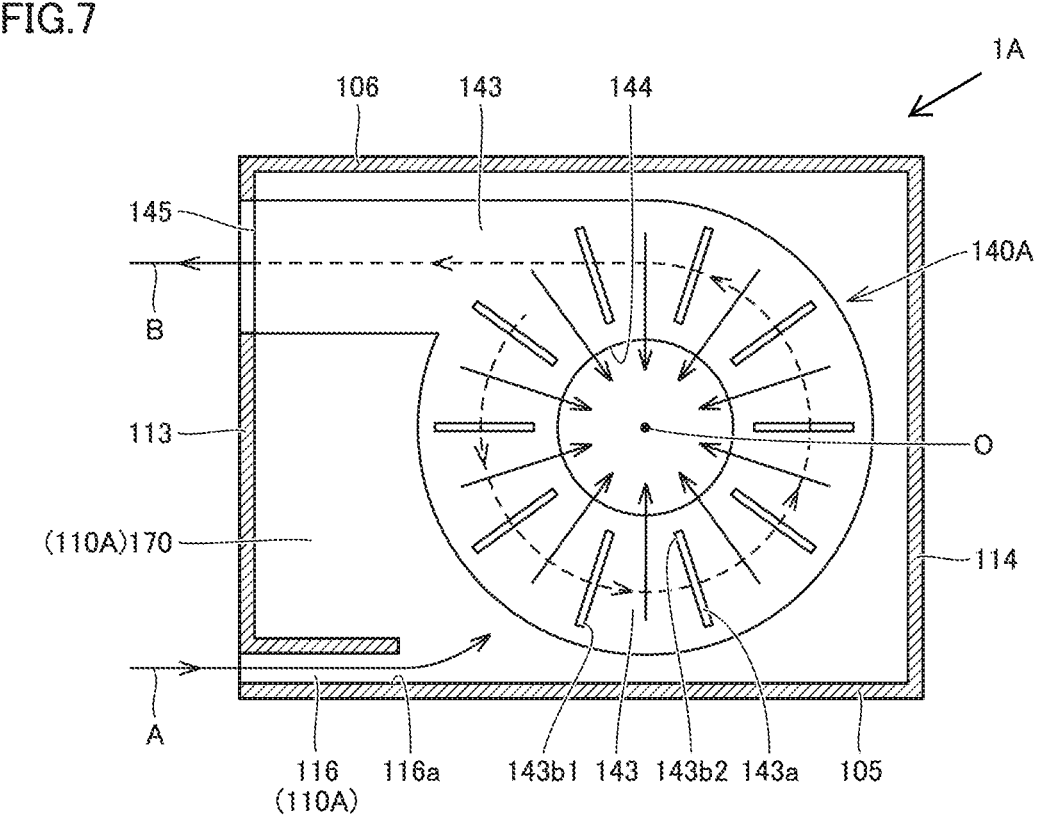
FIG. 7 is an example of a diagram schematically showing a flow of air in an air blower chamber of the CPAP device according to the first embodiment.
Figure 8:
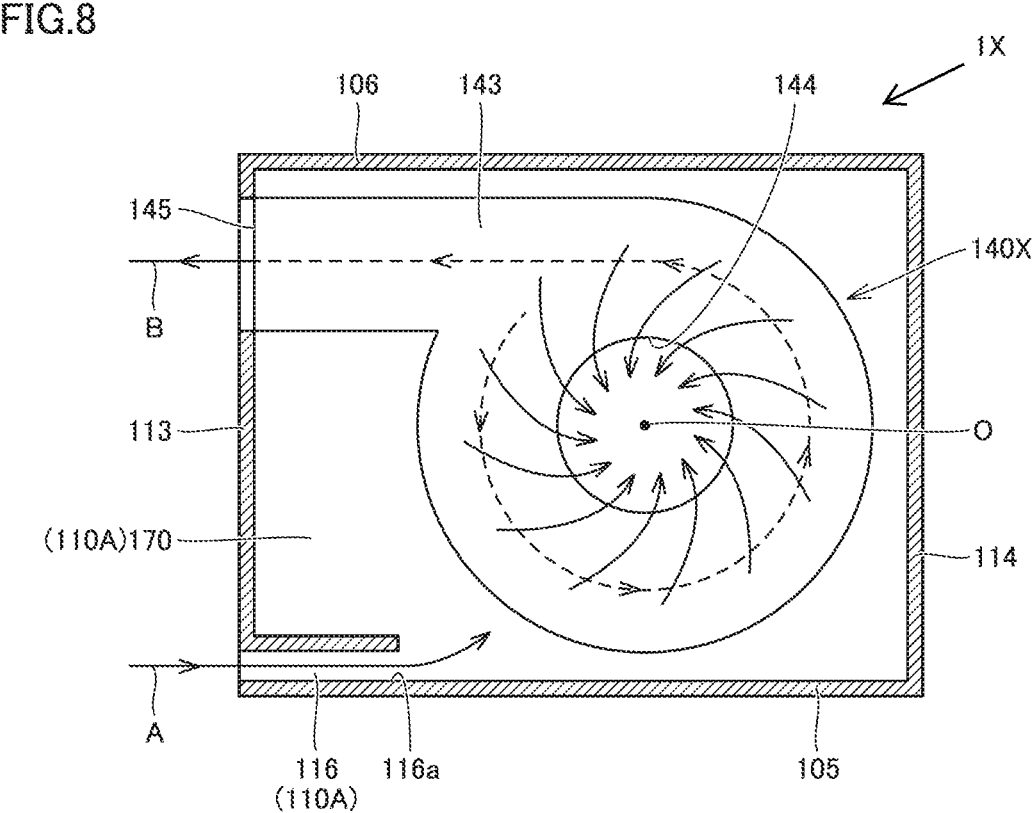
FIG. 8 is an example of a diagram schematically showing a flow of air in an air blower chamber of a CPAP device according to a comparative example.

FIG. 7 is a diagram schematically showing a flow of air in the air blower chamber of the CPAP device according to the present embodiment, and FIG. 8 is a diagram schematically showing a flow of air in an air blower chamber of the CPAP device according to the comparative example.

As shown in FIG. 8, a CPAP device 1X according to the comparative example differs from CPAP device 1A according to the present embodiment only in that an air blower 140X in which the plurality of flow adjustment plates 143a are not provided on the top plate portion of casing 143 is provided instead of air blower 140A.

As with CPAP device 1A according to the present embodiment, when air blower 140X is operated in CPAP device 1X according to the comparative example, air having flown into air blower chamber 117 via introduction port 116a flows into suction port 144 provided in casing 143 of air blower 140X, and is then discharged from discharge port 145 provided in casing 143 of air blower 140X.

In this occasion, air having entered the space between the top plate portion of casing 143 of air blower 140X and upper cover 120 becomes a swirl flow and flows into suction port 144 as shown in the figure. Due to the occurrence of swirl flows, air reaches suction port 144 by way of a detour, rather than reaching suction port 144 in the shortest distance. In this occasion, the flow rate of the air flowing into suction port 144 is accelerated, resulting in an increased pressure loss. Therefore, the air sending performance of air blower 140X is decreased by the increased pressure loss.

Further, due to the occurrence of swirl flows, a backflow may locally occur in the vicinity of suction port 144. The occurrence of such a local backflow induces the turbulence of airflow (i.e., non-uniform airflows in the vicinity of suction port 144), thus resulting in an increased noise.

On the other hand, as shown in FIG. 7, in CPAP device 1A according to the present embodiment, the portion of air sending path 110 communicating with suction port 144 is divided into the plurality of flow paths 143b by the plurality of flow adjustment plates 143a provided on the top plate portion of casing 143 of air blower 140A. Hence, the occurrence of swirl flows is suppressed when air passes through the plurality of flow paths 143b, and air reaches suction port 144 in the shortest distance as shown in the FIG. 7.

Accordingly, air is not accelerated unnecessarily in the vicinity of suction port 144 and the occurrence of local backflows can be suppressed, thus attaining a uniform airflow in the vicinity of suction port 144. This makes it possible to dramatically suppress the occurrence of a pressure loss and to significantly suppress the occurrence of noises.

Therefore, CPAP device 1A according to the present embodiment can be downsized as compared with the conventional device while ensuring the operational quietness. Also, since air can be efficiently sent, its power consumption can be reduced.

1.1. The First Modification

Figure 9:
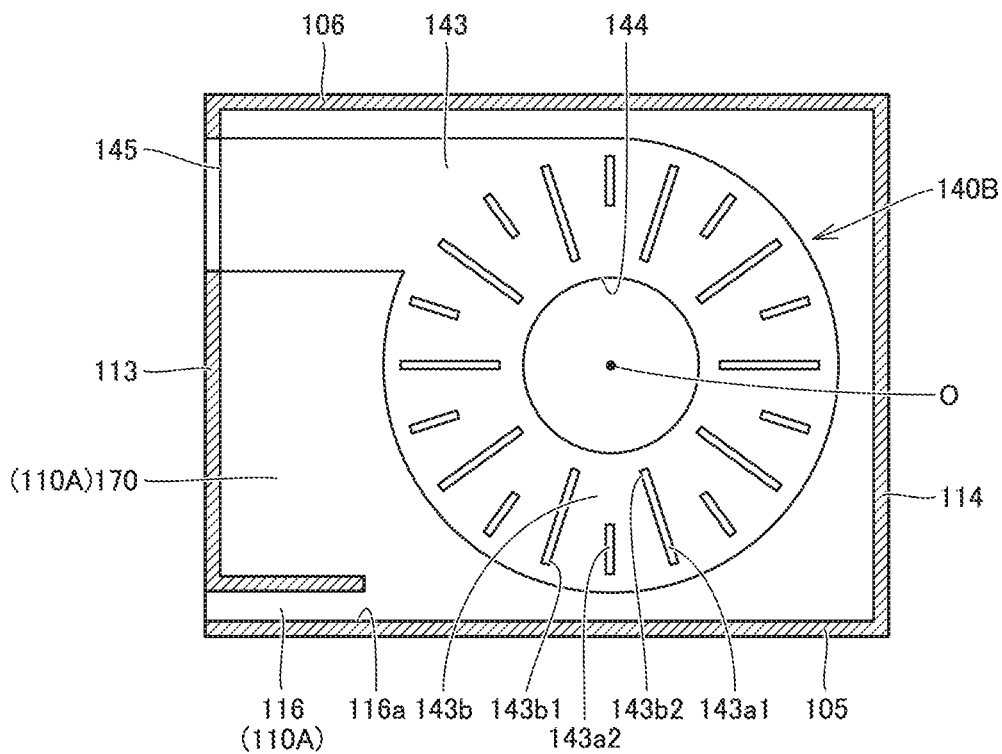
FIG. 9 is an example of a schematic diagram showing a configuration of a flow adjustment portion of a CPAP device according to a first modification.

FIG. 9 is a schematic diagram showing a configuration of a flow adjustment portion of a CPAP device according to a first modification in association with the first embodiment. Hereinafter, the CPAP device according to the first modification based on the first embodiment will be described with reference to FIG. 9.

As shown in FIG. 9, the CPAP device according to the first modification includes an air blower 140B instead of air blower 140A. Air blower 140B is different from air blower 140A in terms of the configuration of the flow adjustment portion. Air blower 140B is configured such that a plurality of main flow adjustment plates 143a1 and a plurality of additional flow adjustment plates 143a2 protruding toward the upper cover 120 side are provided on the top plate portion of casing 143, and the flow adjustment portion is constituted of the plurality of main flow adjustment plates 143a1 and the plurality of additional flow adjustment plates 143a2.

Each of main flow adjustment plates 143a1 has a relatively long length in the direction orthogonal to the rotation axis O, and each of additional flow adjustment plates 143a2 has a relatively short length in the direction orthogonal to the rotation axis O. Main flow adjustment plates 143a1 and additional flow adjustment plates 143a2 are alternately disposed around the rotation axis O. The respective outer end portions thereof are located concentrically with respect to the rotation axis O. Thus, each additional flow adjustment plate 143a2 partitions an upstream side portion (i.e., a portion close to the outer end portion) of a flow path 143b defined by a pair of main flow adjustment plates 143a1 adjacent to each other.

In the CPAP device according to the first modification, main flow adjustment plates 143a1 and additional flow adjustment plates 143a2 are provided at equal intervals around the rotation axis O. Thus, first open ends 143b1 of the plurality of flow paths 143b have the same opening area, and second open ends 143b2 of the plurality of flow paths 143b have the same opening area.

With such a configuration, as with the first embodiment described above, the device can be downsized as compared with the conventional device while ensuring the operational quietness. Further, with the above-described configuration being employed, flow path 143b formed between main flow adjustment plates 143a1 is subdivided by providing additional flow adjustment plate 143a2 in addition to main flow adjustment plate 143a1, thereby exhibiting a higher flow adjustment effect. Therefore, the occurrence of swirl flows can be further suppressed when air passes through the plurality of flow paths 143b.

On the other hand, when additional flow adjustment plate 143a2 has a length equal to that of main flow adjustment plate 143a1, the opening area of second open end 143b2 is decreased more than necessary to increase flow path resistance at that portion, thus resulting in an increased pressure loss. However, the occurrence of such a problem can be prevented by providing additional flow adjustment plate 143a2 with a length shorter than that of main flow adjustment plate 143a1 and disposing additional flow adjustment plate 143a2 at the upstream side portion of each of the plurality of flow paths 143b as described above.

In the first modification, it has been illustrated that main flow adjustment plates 143a1 and additional flow adjustment plates 143a2 are alternately disposed one by one; however, main flow adjustment plates 143a1 and additional flow adjustment plates 143a2 are not necessarily alternately disposed one by one, and one or a plurality of additional flow adjustment plates 143a2 may be disposed between a pair of adjacent main flow adjustment plates 143a1. Also with such a configuration, the occurrence of swirl flows can be suppressed while suppressing increased pressure loss in the vicinity of suction port 144.

2. The Second Embodiment

Figure 10:
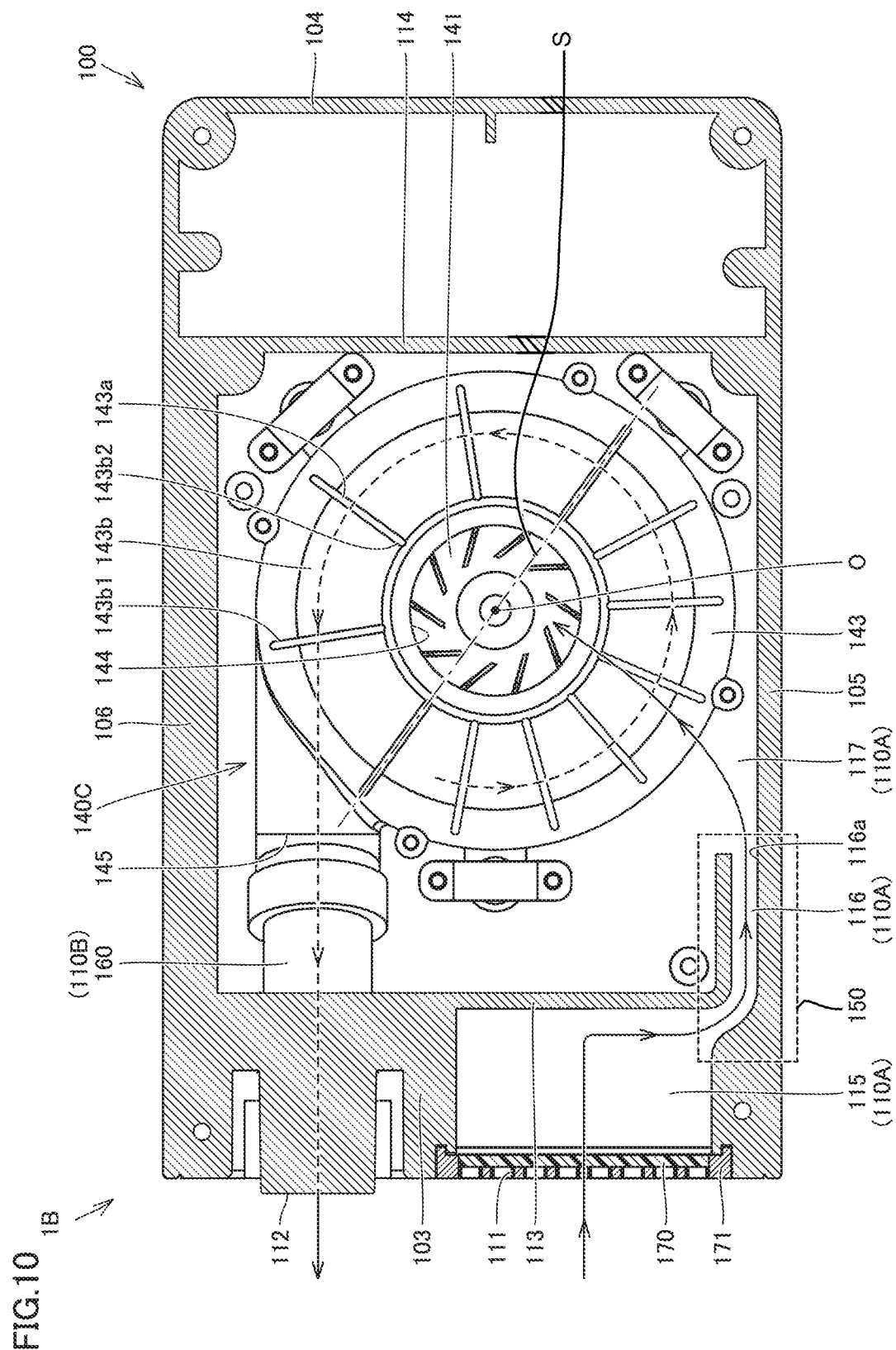
FIG. 10 is an example of a schematic cross sectional view of a CPAP device according to a second embodiment.
Figure 11:
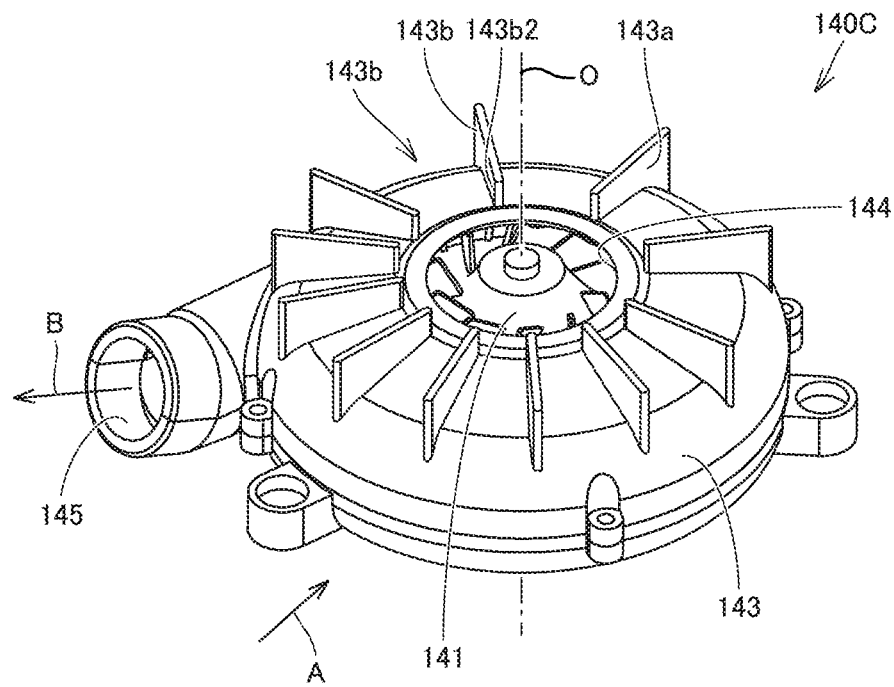
FIG. 11 is an example of a perspective view of an air blower shown in FIG. 10.
Figure 12:
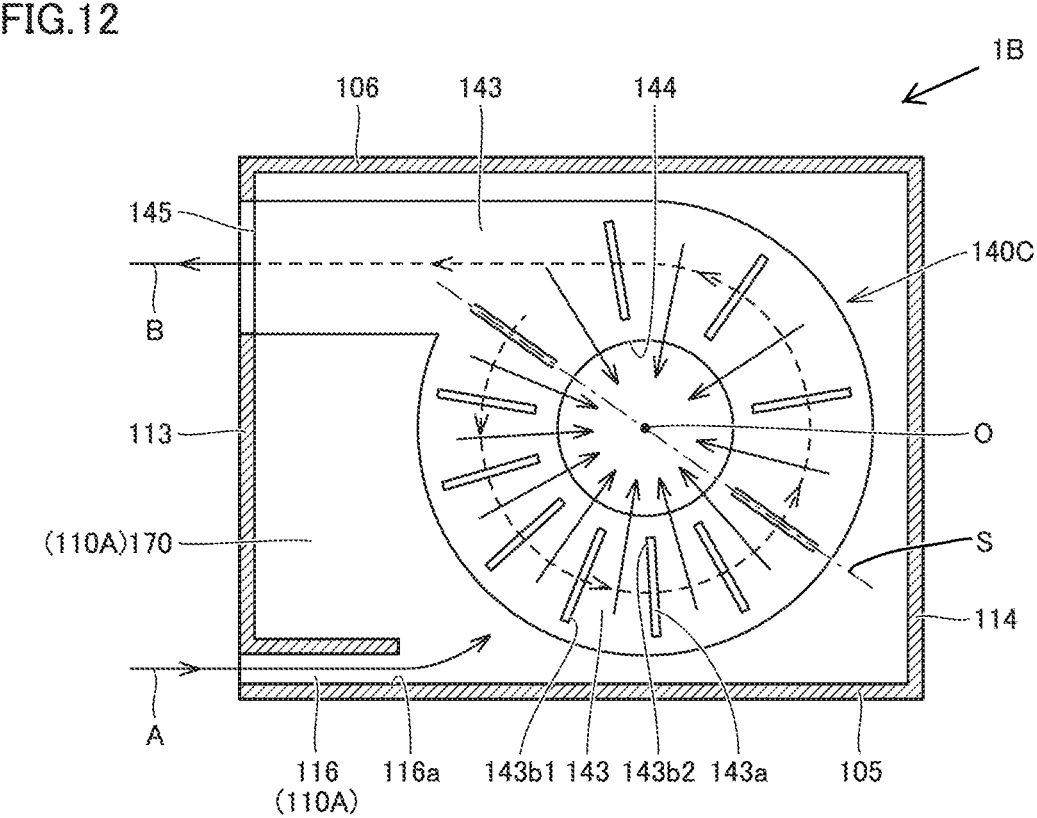
FIG. 12 is an example of a diagram schematically showing a flow of air in an air blower chamber of the CPAP device according to the second embodiment.

FIG. 10 is a schematic cross sectional view of a CPAP device according to a second embodiment of the present disclosure, and FIG. 11 is a perspective view of the air blower shown in FIG. 10. FIG. 12 is a diagram schematically showing a flow of air in an air blower chamber of the CPAP device shown in FIG. 10. Hereinafter, a CPAP device 1B according to the second embodiment will be described with reference to FIGS. 10 to 12.

As shown in FIG. 10 to FIG. 12, CPAP device 1B according to the present embodiment includes an air blower 140C instead of air blower 140A of CPAP device 1A according to the first embodiment. Air blower 140C is different from air blower 140A in terms of the configuration of the flow adjustment portion. As with air blower 140A, air blower 140C is configured such that a plurality of flow adjustment plates 143a protruding toward the upper cover 120 side are provided on the top plate portion of casing 143, and the flow adjustment portion is constituted of the plurality of flow adjustment plates 143a; however, the layout of the plurality of flow adjustment plates 143a is different from that in air blower 140A.

Specifically, in air blower 140C, intervals between adjacent flow adjustment plates 143a are different with respect to the reference plane S that includes the rotation axis O and that is substantially orthogonal to a main flow direction of air introduced from introduction port 116a (i.e., the direction of arrow A shown in FIG. 11). That is, an interval between flow adjustment plates of the plurality of flow adjustment plates 143a on the introduction port 116a side when seen from suction port 144 is smaller than an interval between flow adjustment plates of the plurality of flow adjustment plates 143a on the side opposite to the introduction port 116a side when seen from suction port 144.

Thus, the opening area of first open end 143b1 of each flow path of the plurality of flow paths 143b on the introduction port 116a side when seen from suction port 144 is smaller than the opening area of first open end 143b1 of each flow path of the plurality of flow paths 143b on the side opposite to the introduction port 116a side when seen from suction port 144.

With such a configuration, as shown in FIG. 12, the flow path resistance of a flow path which is closer to introduction port 116a and into which air is more likely to flow (i.e., a flow path of the plurality of flow paths 143b close to introduction port 116a relative to the reference plane S) is larger than the flow path resistance of a flow path which is farther away from introduction port 116a and into which air is less likely to flow (i.e., a flow path of the plurality of flow paths 143b far away from introduction port 116a relative to the reference plane S).

Therefore, by employing the above-described configuration, the device can be downsized as compared with the conventional device while ensuring quietness as with the first embodiment described above, and an airflow can be more uniform in the vicinity of suction port 144, with the result that generation of noise can be further suppressed.

2. 1. The Second Modification

Figure 13:
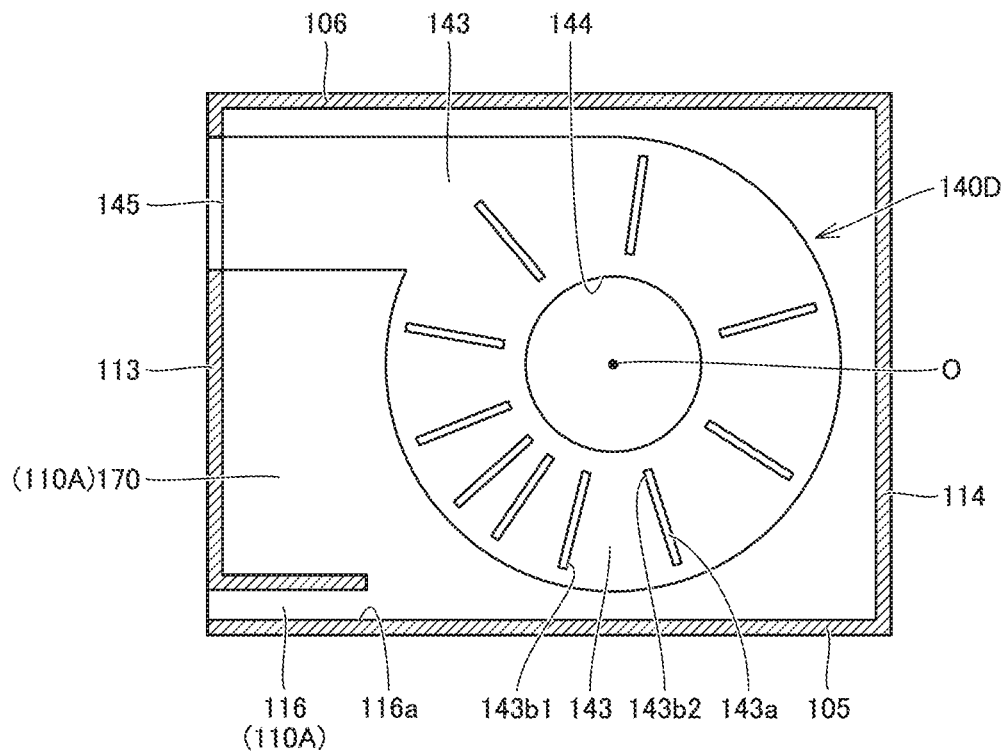
FIG. 13 is an example of a schematic diagram showing a configuration of a flow adjustment portion of a CPAP device according to a second modification.

FIG. 13 is a schematic diagram showing a configuration of a flow adjustment portion of a CPAP device according to a second modification. Hereinafter, the CPAP device according to the second modification based on the second embodiment will be described with reference to FIG. 13.

As shown in FIG. 13, the CPAP device according to the second modification includes an air blower 140D instead of air blower 140C described above. Air blower 140D is different from air blower 140C in terms of the configuration of the flow adjustment portion. As with air blower 140C, air blower 140D is configured such that a plurality of flow adjustment plates 143a protruding toward the upper cover 120 side are provided on the top plate portion of casing 143, and the flow adjustment portion is constituted of the plurality of flow adjustment plates 143a; however, the layout of the plurality of flow adjustment plates 143a is different from that in air blower 140C.

Specifically, air blower 140D is configured such that intervals between adjacent flow adjustment plates 143a become smaller as flow adjustment plates 143a are closer to introduction port 116a. Thus, a first open end 143b1 provided in a flow path 143b of the plurality of flow paths 143b at a shorter distance from introduction port 116a has a smaller opening area.

With such a configuration, the device can be downsized as compared with the conventional device while ensuring quietness as with the second embodiment described above, and the flow path resistances of the plurality of flow paths 143b are changed gradually in the circumferential direction of suction port 144. Hence, an airflow can be more uniform in the vicinity of suction port 144 than in the case of the second embodiment, with the result that generation of noise can be further suppressed.

2.2. The Third Modification

Figure 14:
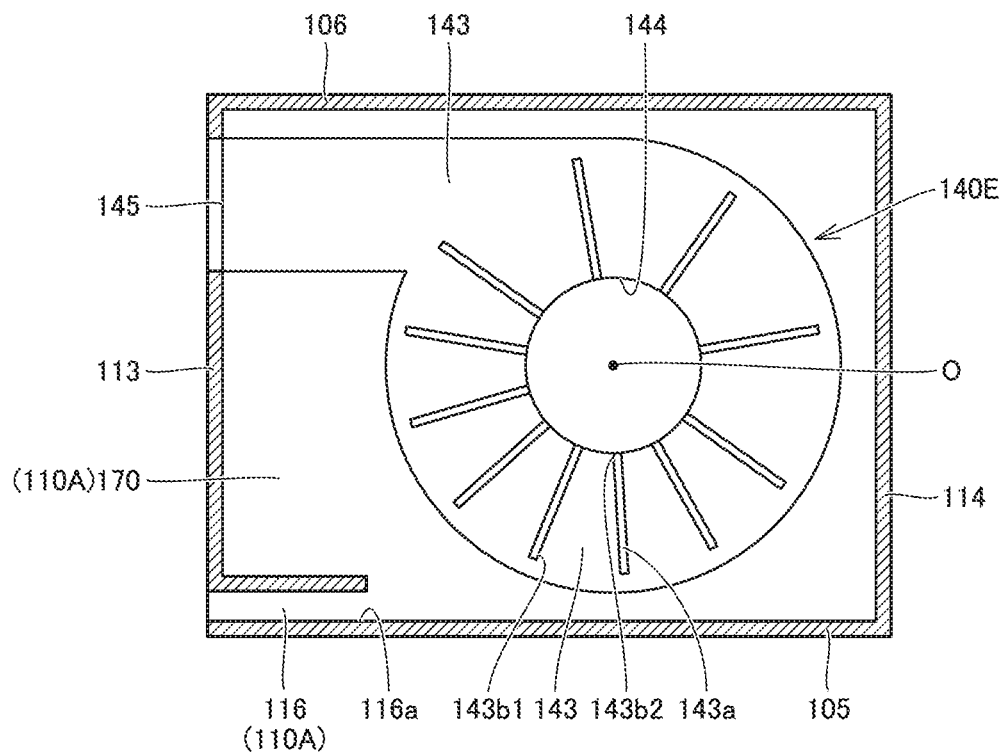
FIG. 14 is an example of a schematic diagram showing a configuration of a flow adjustment portion of a CPAP device according to a third modification.

FIG. 14 is a schematic diagram showing a configuration of a flow adjustment portion of a CPAP device according to a third modification. Hereinafter, the CPAP device according to the third modification based on the second embodiment will be described with reference to FIG. 14.

As shown in FIG. 14, the CPAP device according to the third modification includes an air blower 140E instead of air blower 140C described above. Air blower 140E is different from air blower 140C in terms of the configuration of the flow adjustment portion. As with air blower 140C, air blower 140E is configured such that a plurality of flow adjustment plates 143a protruding toward the upper cover 120 side are provided on the top plate portion of casing 143, and the flow adjustment portion is constituted of the plurality of flow adjustment plates 143a; however, the shape of each of the plurality of flow adjustment plates 143a is different from that in air blower 140C.

Specifically, in air blower 140E, the inner end portion of each of the plurality of flow adjustment plates 143a (i.e., the end portion thereof on the suction port 144 side) reaches the outer edge of suction port 144. Thus, each of the plurality of flow paths 143b extends to reach the outer edge of suction port 144.

With such a configuration, the device can be downsized as compared with the conventional device while ensuring quietness as with the second embodiment described above, and the occurrence of swirl flows can be more securely suppressed in the vicinity of suction port 144 to further securely suppress the occurrence of a pressure loss.

2.3. The Fourth Modification

Figure 15:
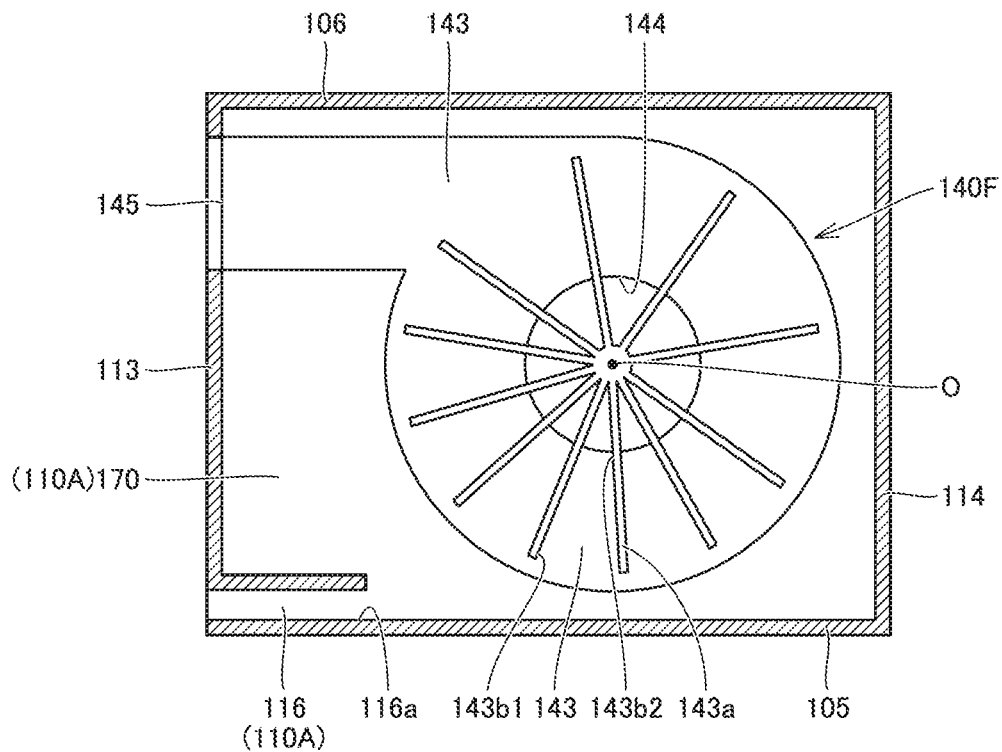
FIG. 15 is an example of a schematic diagram showing a configuration of a flow adjustment portion of a CPAP device according to a fourth modification.

FIG. 15 is a schematic diagram showing a configuration of a flow adjustment portion of a CPAP device according to a fourth modification. Hereinafter, the CPAP device according to the fourth modification based on the second embodiment will be described with reference to FIG. 15.

As shown in FIG. 15, the CPAP device according to the fourth modification includes an air blower 140F instead of air blower 140C described above. Air blower 140F is different from air blower 140C in terms of the configuration of the flow adjustment portion. As with air blower 140C, air blower 140F is configured such that a plurality of flow adjustment plates 143a protruding toward the upper cover 120 side are provided on the top plate portion of casing 143, and the flow adjustment portion is constituted of the plurality of flow adjustment plates 143a; however, the shape of each of the plurality of flow adjustment plates 143a is different from that in air blower 140C.

Specifically, in air blower 140F, the inner end portions of the plurality of flow adjustment plates 143a reach a space above suction port 144, and the inner end portions of the plurality of flow adjustment plates 143a are connected to one another at a portion that crosses the rotation axis O.

With such a configuration, the device can be downsized as compared with the conventional device while ensuring quietness as with the second embodiment described above, and the mechanical strength of casing 143 of air blower 140A can be improved, resulting in improved durability.

2.4. The Fifth Modification

Figure 16:
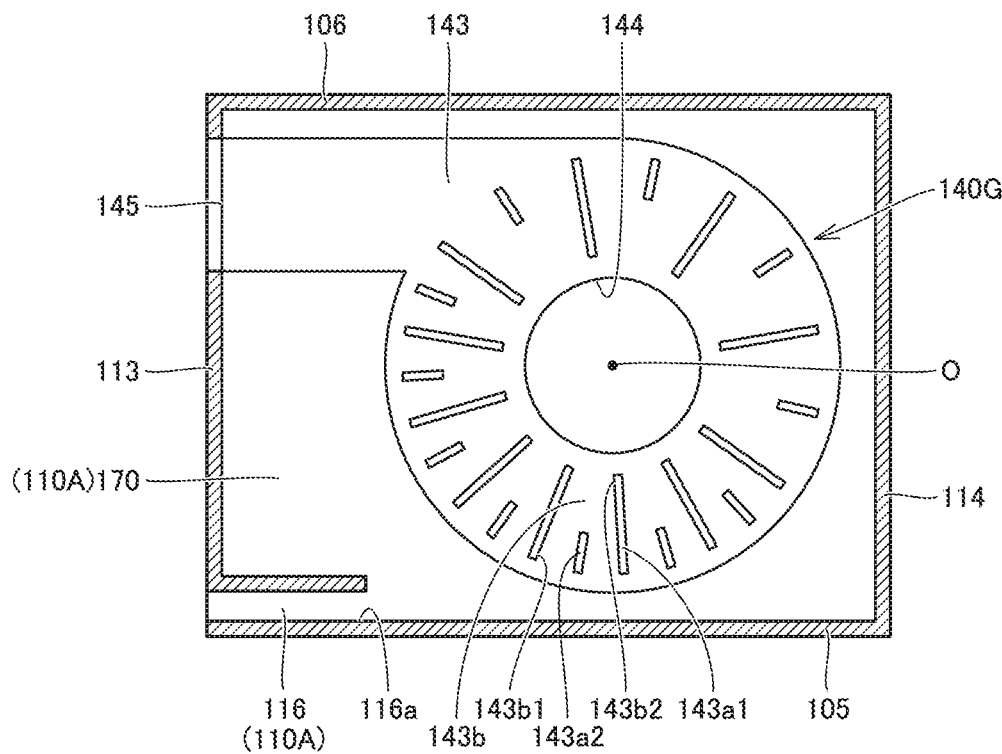
FIG. 16 is an example of a schematic diagram showing a configuration of a flow adjustment portion of a CPAP device according to a fifth modification.

FIG. 16 is a schematic diagram showing a configuration of a flow adjustment portion of a CPAP device according to a fifth modification. Hereinafter, the CPAP device according to the fifth modification based on the second embodiment will be described with reference to FIG. 16.

As shown in FIG. 16, the CPAP device according to the fifth modification includes an air blower 140G instead of air blower 140C described above. Air blower 140G is different from air blower 140C in terms of the configuration of the flow adjustment portion. Air blower 140G is configured such that a plurality of main flow adjustment plates 143a1 and a plurality of additional flow adjustment plates 143a2 protruding toward the upper cover 120 side are provided on the top plate portion of casing 143, and the flow adjustment portion is constituted of the plurality of main flow adjustment plates 143a1 and the plurality of additional flow adjustment plates 143a2.

Here, as with the first modification described above, each of main flow adjustment plates 143a1 has a relatively long length in the direction orthogonal to the rotation axis O, and each of additional flow adjustment plates 143a2 has a relatively short length in the direction orthogonal to the rotation axis O. As with the first modification, main flow adjustment plates 143a1 and additional flow adjustment plates 143a2 are alternately disposed around the rotation axis O, and the respective outer end portions thereof are located concentrically with respect to the rotation axis O.

With such a configuration, the device can be downsized as compared with the conventional device while ensuring quietness as with the second embodiment described above, a higher flow adjustment effect can be achieved by providing additional flow adjustment plate 143a2 in addition to main flow adjustment plate 143a1, and increased a pressure loss by a subdivided flow path 143b formed between main flow adjustment plates 143a1 can be suppressed.

2.5. The Sixth Modification

Figure 17:
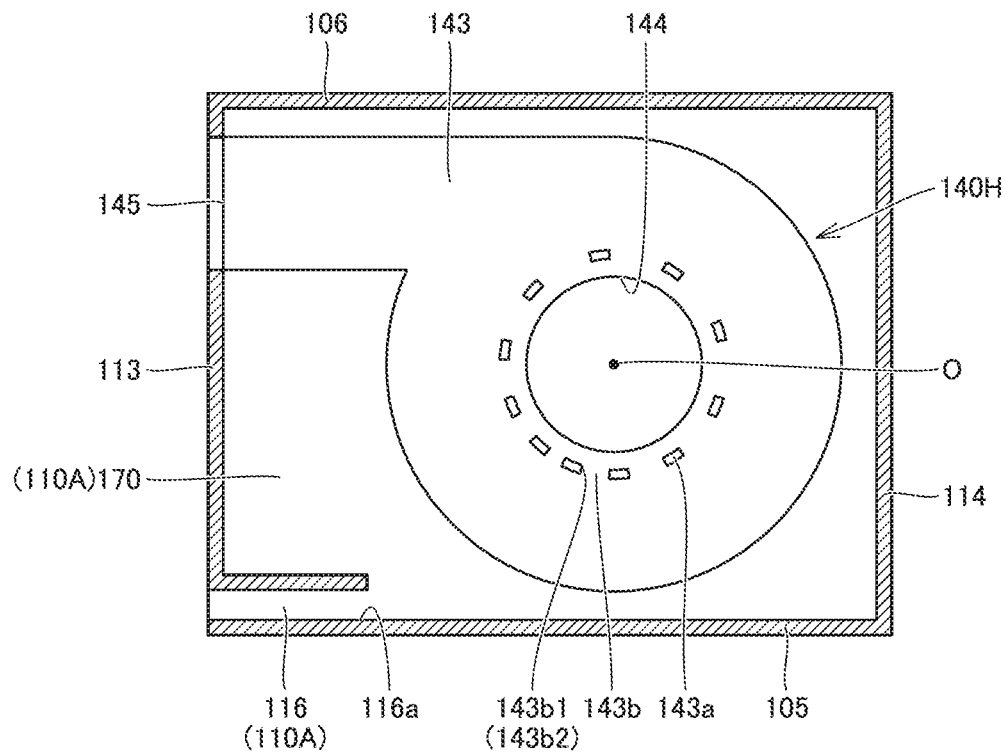
FIG. 17 is an example of a schematic diagram showing a configuration of a flow adjustment portion of a CPAP device according to a sixth modification.

FIG. 17 is a schematic diagram showing a configuration of a flow adjustment portion of a CPAP device according to a sixth modification. Hereinafter, the CPAP device according to the sixth modification based on the second embodiment will be described with reference to FIG. 17.

As shown in FIG. 17, the CPAP device according to the six modification includes an air blower 140H instead of air blower 140C described above. Air blower 140H is different from air blower 140C in terms of the configuration of the flow adjustment portion. Air blower 140H is configured such that a plurality of flow adjustment plates 143a protruding toward the upper cover 120 side are provided on the top plate portion of casing 143, and the flow adjustment portion is constituted of the plurality of flow adjustment plates 143a; however, the shape of each of the plurality of flow adjustment plates 143a is different from that in air blower 140C.

Specifically, in air blower 140H, each of the plurality of flow adjustment plates 143a has a curved plate-like shape extending along the circumferential direction of suction port 144, and the plurality of flow adjustment plates 143a are provided at locations in the vicinity of suction port 144 (i.e., locations close to the inner circumferential edge of the annular top plate portion of casing 143 of air blower 140H).

Also with such a configuration, an effect corresponding to that of the above-described second embodiment can be obtained, the occurrence of swirl flows can be suppressed in the vicinity of suction port 144, and an airflow can be uniform in the vicinity of suction port 144, with the result that the device can be downsized as compared with the conventional device while ensuring quietness during the operation.

2.6. The Seventh Modification

Figure 18:
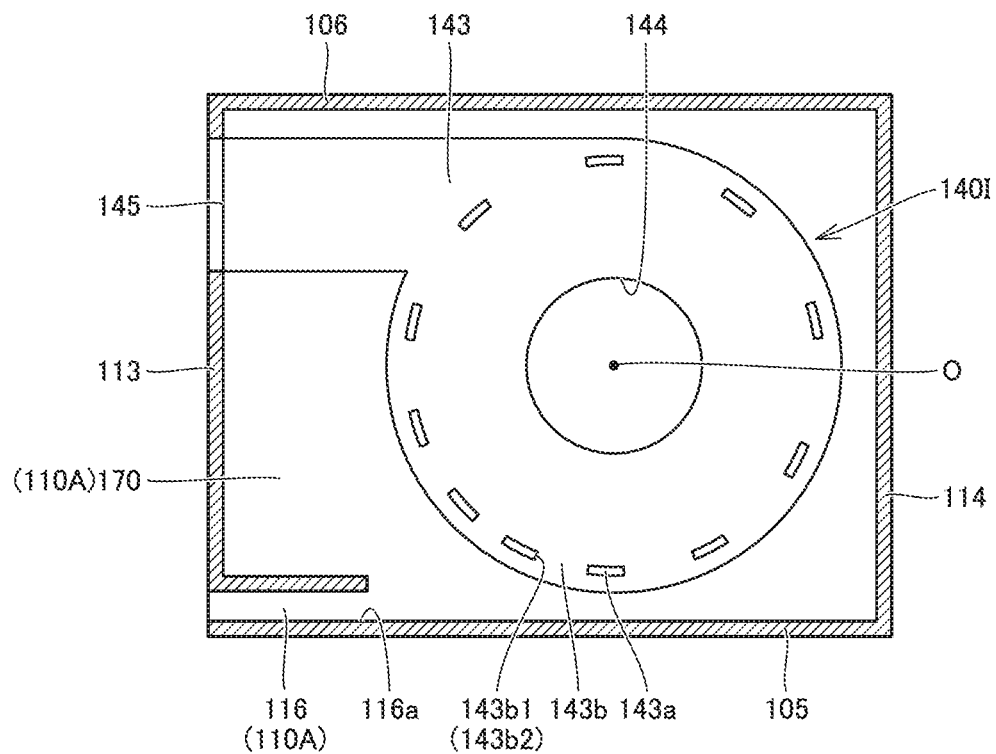
FIG. 18 is an example of a schematic diagram showing a configuration of a flow adjustment portion of a CPAP device according to a seventh modification.

FIG. 18 is a schematic diagram showing a configuration of a flow adjustment portion of a CPAP device according to a seventh modification. Hereinafter, the CPAP device according to the seventh modification based on the second embodiment will be described with reference to FIG. 18.

As shown in FIG. 18, the CPAP device according to the seventh modification includes an air blower 140I instead of air blower 140C described above. Air blower 140I is different from air blower 140C in terms of the configuration of the flow adjustment portion. Air blower 140I is configured such that a plurality of flow adjustment plates 143a protruding toward the upper cover 120 side are provided on the top plate portion of casing 143, and the flow adjustment portion is constituted of the plurality of flow adjustment plates 143a; however, the shape of each of the plurality of flow adjustment plates 143a is different from that in air blower 140C.

Specifically, in air blower 140I, each of the plurality of flow adjustment plates 143a has a curved plate-like shape extending along the circumferential direction of suction port 144, and the plurality of flow adjustment plates 143a are provided at locations relatively far away from suction port 144 (i.e., locations close to the outer circumferential edge of the annular top plate portion of casing 143 of air blower 140I).

Also with such a configuration, an effect corresponding to that of the above-described second embodiment can be obtained, the occurrence of swirl flows can be suppressed in the vicinity of suction port 144, and an airflow can be uniform in the vicinity of suction port 144, with the result that the device can be downsized as compared with the conventional device while ensuring quietness.

2.7. The Eighth Modification

Figure 19:
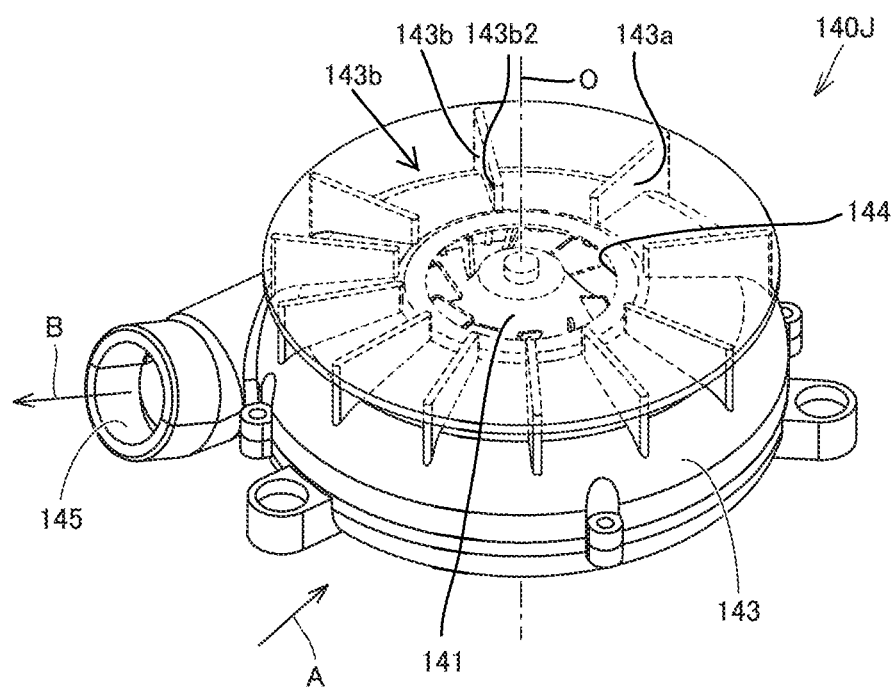
FIG. 19 is an example of a perspective view of an air blower of a CPAP device according to an eighth modification.

FIG. 19 is a perspective view of an air blower of a CPAP device according to an eighth modification. Hereinafter, the CPAP device according to the eighth modification based on the second embodiment will be described with reference to FIG. 19.

The CPAP device according to the eighth modification includes an air blower 140J having a configuration shown in FIG. 19, instead of air blower 140C described above. Air blower 140J is different from air blower 140C in terms of the configuration of the flow adjustment portion. Air blower 140J is configured such that a plurality of flow adjustment plates 143a protruding toward the upper cover 120 side and an auxiliary flow adjustment plate 143c covering flow adjustment plates 143a are provided on the top plate portion of casing 143, and the flow adjustment portion is constituted of the plurality of flow adjustment plates 143a and auxiliary flow adjustment plate 143c.

Auxiliary flow adjustment plate 143c has a flat, circular plate-like shape orthogonal to the rotation axis O, and is located on the upper cover 120 side of each of the plurality of flow adjustment plates 143a (i.e., the side opposite to the side on which impeller 141 is located when seen from the plurality of flow adjustment plates 143a). Thus, auxiliary flow adjustment plate 143c closes each of the plurality of flow paths 143b at the location on the upper cover 120 side.

Also with such a configuration, an effect similar to that in the above-described second embodiment can be obtained, the occurrence of swirl flows can be suppressed in the vicinity of suction port 144, and an airflow can be uniform in the vicinity of suction port 144, with the result that the device can be downsized as compared with the conventional device while ensuring quietness.

Here, in the case of employing such a configuration as the one in the eighth modification, the flow adjustment effect at the flow adjustment portion can be securely obtained even when the portion facing the top plate portion of casing 143 of air blower 140J (i.e., the facing wall portion) in the wall portions constituting air blower chamber 117 has a non-flat shape. In other words, regardless of the shape of air blower chamber 117, the device can be downsized as compared with the conventional device while ensuring quietness.

3. The Third Embodiment

Figure 20:
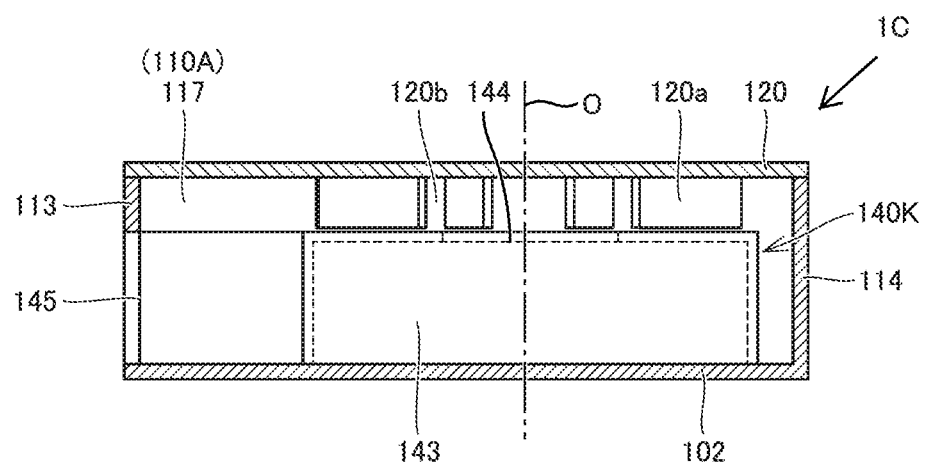
FIG. 20 is an example of a schematic cross sectional view of an air blower chamber of a CPAP device according to a third embodiment.

FIG. 20 is a schematic cross sectional view of an air blower chamber of a CPAP device according to a third embodiment of the present disclosure. Hereinafter, a CPAP device 1C according to the present embodiment will be described with reference to FIG. 20.

As shown in FIG. 20, CPAP device 1C according to the third embodiment includes an air blower 140K instead of air blower 140A of CPAP device 1A according to the first embodiment. No flow adjustment portion is provided in air blower 140K, and a flow adjustment portion is provided on upper cover 120 constituting a part of the wall portions defining air blower chamber 117.

Specifically, in CPAP device 1C, a plurality of flow adjustment plates 120a protruding toward the top plate portion side of casing 143 are provided on upper cover 120 at a portion facing the top plate portion of casing 143 of air blower 140K, and the flow adjustment portion is constituted of the plurality of flow adjustment plates 120a. The flow adjustment portion constituted of the plurality of flow adjustment plates 120a adjusts a flow of air suctioned from the outside of casing 143 of air blower 140K into casing 143 via suction port 144.

Specifically, the plurality of flow adjustment plates 120a are provided to extend radially with respect to the rotation axis O, and are therefore located to surround suction port 144. By providing the plurality of flow adjustment plates 120a, a space between the top plate portion of casing 143 of air blower 140K and upper cover 120 is partitioned into a plurality of flow paths 120b arranged side by side around the rotation axis O.

Here, the plurality of flow adjustment plates 120a are provided on upper cover 120 unlike the plurality of flow adjustment plates 143a in the first embodiment; however, the other configurations (the shapes, sizes, layouts when seen along the rotation axis O, and the like) are basically the same as those of the plurality of flow adjustment plates 143a.

Also with such a configuration, an effect similar to the first embodiment described above can be obtained, the occurrence of swirl flows can be suppressed in the vicinity of suction port 144, and an airflow can be uniform in the vicinity of suction port 144, with the result that the device can be downsized as compared with the conventional device while ensuring quietness.

4. Verification Test

The following describes a verification test performed to verify what degree of effect is obtained by using each of the CPAP devices according to the present embodiment and modifications thereof. In the verification test, the CPAP device according to the first modification based on the first embodiment and the CPAP device according to the comparative example described above were used as models. An analysis was performed through simulation as to what pressure change occurred at each location in the air sending path and what degree of air sending performance was attained in each of the CPAP devices as a whole when the air blower was driven in the CPAP device.

Here, in order to check only the effect attained by providing the flow adjustment portion, the above-described models were made different from each other only in terms of the configuration of the air blower and the other portions had the same configurations. The difference between the configurations of the air blowers in the both models lies only in that main flow adjustment plates 143a1 and additional flow adjustment plates 143a2 described above are provided as the flow adjustment portion in the CPAP device according to the first modification, as shown in FIG. 9, whereas main flow adjustment plate 143a1 and additional flow adjustment plate 143a2 are not provided in the CPAP device according to the comparative example, as shown in FIG. 8. It should be noted that the size of the clearance between the top plate portion of the casing of the air blower and the upper cover was 3 mm at minimum in each of the models. In the CPAP device according to the first modification, each of the heights of main flow adjustment plates 143a1 and additional flow adjustment plates 143a2 was 3 mm, which is the same as the size of the clearance.

Figure 21A:
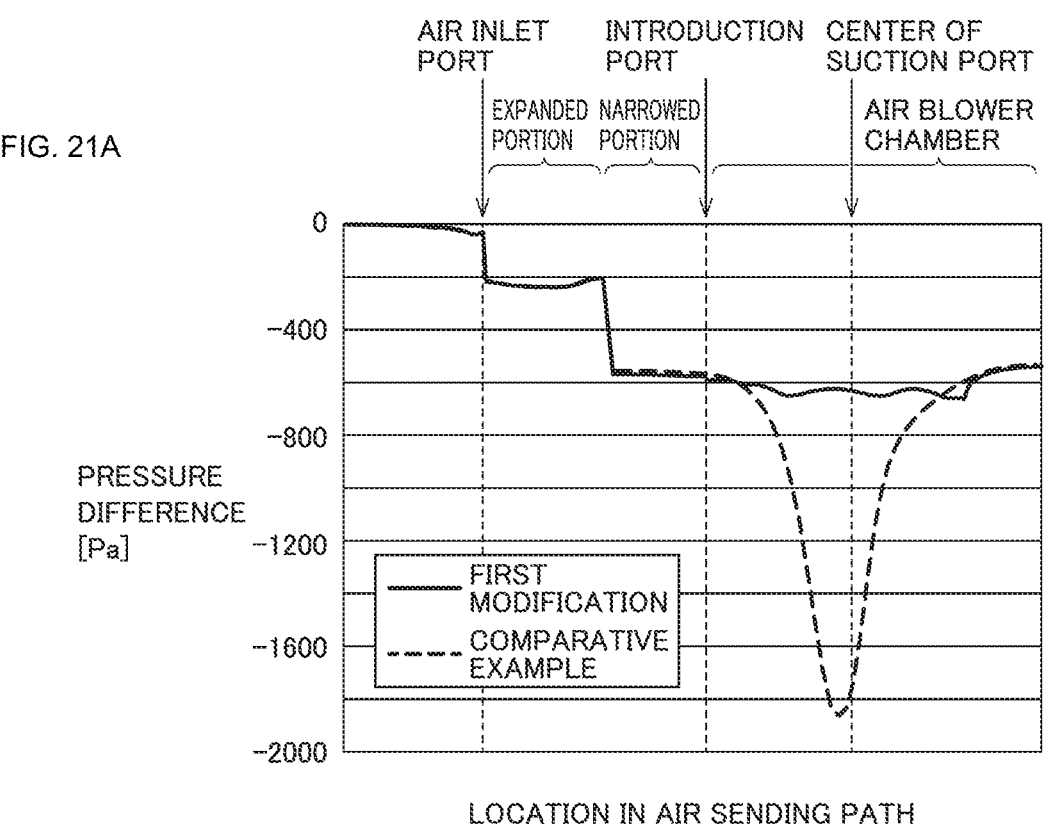
FIGS. 21A and 21B show example graphs illustrating results of a verification test.
Figure 21B:
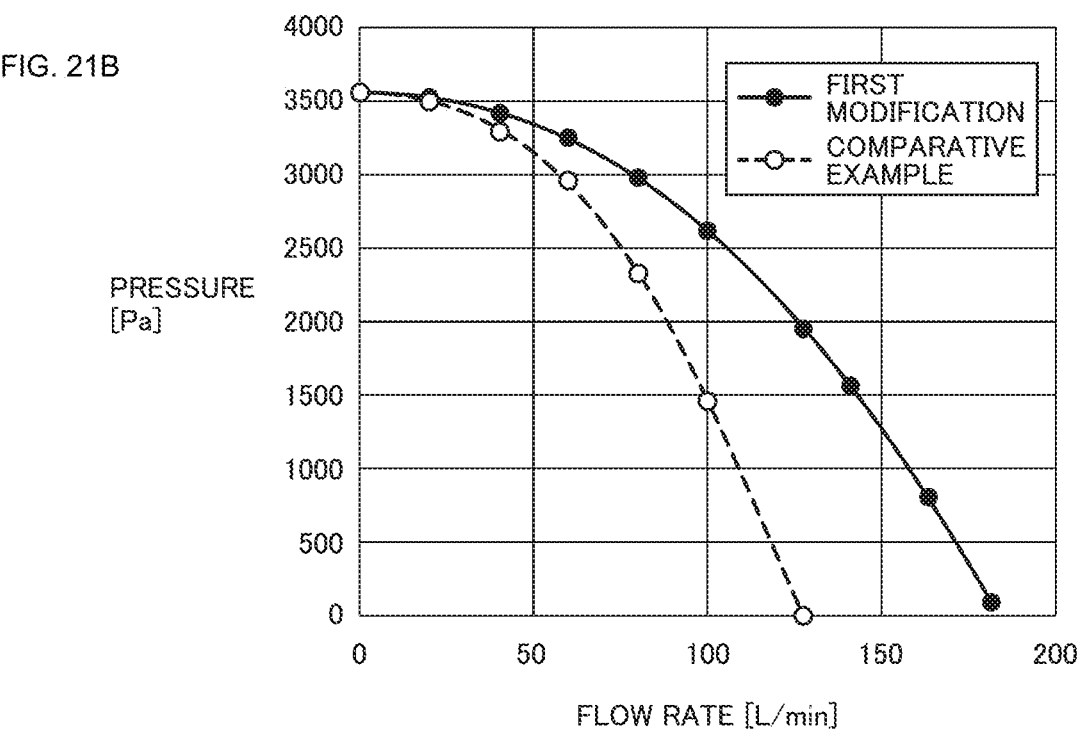

FIGS. 21A and 21B show graphs illustrating results of the verification test. FIG. 21A is a graph showing a pressure change at each location in the air sending path, and FIG. 21B is a graph showing a so-called PQ characteristic representing the air sending performance of each CPAP device as a whole. It should be noted that in the graph shown in FIG. 21A, the vertical axis represents a pressure difference when a pressure at the air inlet port was 0, and the horizontal axis represents a location in the air blower path. In the graph shown in FIG. 21B, the vertical axis represents a pressure at the air outlet port, and the horizontal axis represents a flow rate at the air outlet port.

As shown in FIG. 21A, in the CPAP device according to the comparative example in which no flow adjustment portion is provided, a pressure loss occurs on the downstream side of the air inlet port and the downstream side of the narrowed portion, and a larger pressure loss occurs at a portion leading to the suction port and a portion on the downstream side of the suction port.

On the other hand, in the CPAP device according to the first modification in which the flow adjustment portion is provided, a pressure loss occurs on the downstream side of the air inlet port and the downstream side of the narrowed portion as with the CPAP device according to the comparative example; however, a pressure loss at the portion leading to the suction port and the portion on the downstream side of the suction port is much smaller than that in the CPAP device according to the comparative example.

Moreover, as shown in FIG. 21B, in the CPAP device according to the comparative example in which no flow adjustment portion is provided, the pressure is decreased greatly as the flow rate is increased, whereas in the CPAP device according to the first modification in which the flow adjustment portion is provided, the pressure is significantly less decreased. Hence, the CPAP device according to the first modification can ensure a larger flow rate than that in the CPAP device according to the comparative example while maintaining the pressure.

For example, in a no-load state (i.e., a state in which the pressure of the air inlet port, which is a back pressure of the CPAP device, is an atmospheric pressure with the air blower being non-operational), the flow rate is 128 L/min in the CPAP device according to the comparative example in which no flow adjustment portion is provided, whereas the flow rate is increased to 185 L/min in the CPAP device according to the first modification in which the flow adjustment portion is provided.

When the back pressure is 1500 Pa, the flow rate is 99 L/min in the CPAP device according to the comparative example in which no flow adjustment portion is provided, whereas the flow rate is increased to 143 L/min in the CPAP device according to the first modification in which the flow adjustment portion is provided.

Based on the results of the verification test, it is understandable that by employing the CPAP device according to each of the present embodiment and the modifications thereof, air can be efficiently sent even when the CPAP device is thinned, the rotation speed of the air blower and the size of the air blower do not need to be increased, and the operational quietness can be maintained.

In each of the first to third embodiments and their modifications of the present disclosure, it has been illustratively described that the so-called muffler type silencer constituted of the expanded portion and the narrowed portion arranged side by side in the air sending path is applied as the silencer provided inside the housing; however, the silencer is not limited thereto. As the silencer, each or a combination of various types of conventionally known silencers may be employed. The silencer is not necessarily an essential configuration, and the silencer may not be provided in the housing.

In the first to third embodiments and their modifications of the present disclosure, it has been illustratively described that the air blower chamber is constituted of the portions of the housing and the upper cover installed inside the housing; however, the wall portions constituting the air blower chamber may be constituted of any member(s). For example, the housing may constitute all of the wall portions constituting the air blower chamber, or various types of members installed inside the housing may constitute all of the wall portions constituting the air blower chamber.

Further, the characteristic configurations shown in the first to third embodiments and modifications of the present disclosure can be combined with each other without departing from the gist of the present disclosure.

Thus, the embodiments and modifications disclosed herein are illustrative and non-restrictive in any respect. The technical scope of the present disclosure is defined by the terms of the claims, and is intended to include any modifications within the scope and meaning equivalent to the terms of the claims.

REFERENCE SIGNS LIST 1A to 1C: CPAP device; 2: air tube; 3: mask; 100: housing; 101: top plate; 102: bottom plate; 103: first side plate; 104: second side plate; 105: third side plate; 106: fourth side plate; 110: air sending path; 110A: upstream side flow path portion; 110B: downstream side flow path portion; 111: air inlet port; 112: air outlet port; 113: separation wall; 114: partition wall; 115: expanded portion; 116: narrowed portion; 116a: introduction port; 117: air blower chamber; 120: upper cover; 120a: flow adjustment plate; 120b: flow path; 130: control unit; 131: manipulation unit; 132: flow rate sensor; 133: pressure sensor; 140A to 140K: air blower; 141: impeller; 142: drive motor; 143: casing; 143a: flow adjustment plate; 143a1: main flow adjustment plate; 143a2: additional flow adjustment plate; 143b: flow path; 143b1: first open end; 143b2: second open end; 143c: auxiliary flow adjustment plate; 144: suction port; 145: discharge port; 150: silencer; 160: hose; 170: filter; 171: filter cover; O: rotation axis; S: reference plane.

The invention claimed is:

1. A Continuous Positive Airway Pressure (CPAP) device for sending air suctioned into the CPAP device to an airway of a user, the CPAP device comprising:
an air blower; and
a housing in which an air blower chamber is provided to accommodate the air blower, wherein
the air blower includes an impeller rotatable about a rotation axis, a drive unit that drives to rotate the impeller, and a casing surrounding the impeller,
the casing is provided with a suction port for suctioning air inside the air blower chamber into the casing, and a discharge port for discharging the air inside the casing to outside of the casing,
the suction port is located at a top plate portion overlapping with the rotation axis, the top plate portion being one of a pair of wall portions of the casing, the pair of wall portions sandwiching the impeller in a direction in which the rotation axis extends,
wall portions defining the air blower chamber include a wall portion that is located at a portion not overlapping with the top plate portion when seen along the direction in which the rotation axis extends and that is provided with an introduction port for introducing air outside the housing into the air blower chamber,
the air blower chamber includes a facing wall portion facing the top plate portion with a distance between the facing wall portion and the top plate portion,
in a space between the facing wall portion and the top plate portion, a flow adjustment portion that partitions at least a portion of the space into a plurality of flow paths arranged side by side around the rotation axis is provided,
an outer end portion and an inner end portion of each of the plurality of flow paths in a direction orthogonal to the rotation axis include respectively a first open end and a second open end, the first open end and the second open end being open along the direction orthogonal to the rotation axis,
the flow adjustment portion is provided on the top plate portion to protrude toward the facing wall portion, and
the flow adjustment portion is located to be separated from the facing wall portion.

2. The CPAP device according to claim 1, wherein an opening area of a first open end of a flow path of the plurality of flow paths on the introduction port side when seen from the suction port is smaller than an opening area of a first open end of another flow path of the plurality of flow paths on a side opposite to the introduction port side when seen from the suction port.

3. The CPAP device according to claim 2, wherein a first open end provided in the flow path of the plurality of flow paths at a shorter distance from the introduction port has a smaller opening area than the first open end of the other flow path.

4. The CPAP device according to claim 1, wherein the flow adjustment portion includes a plurality of flow adjustment plates that extend radially with respect to the rotation axis.

5. The CPAP device according to claim 4, wherein an inner end portion of each of the plurality of flow adjustment plates reaches an edge of the suction port.

6. The CPAP device according to claim 4, wherein
the plurality of flow adjustment plates include main flow adjustment plates each having a relatively long length and additional flow adjustment plates each having a relatively short length, and
one or a plurality of the additional flow adjustment plates are disposed between adjacent main flow adjustment plates.

7. The CPAP device according to claim 4, wherein the flow adjustment portion further includes an auxiliary flow adjustment plate in a form of a plate, the auxiliary flow adjustment plate being located on the facing wall portion side of each of the plurality of flow adjustment plates, the auxiliary flow adjustment plate closing each of the plurality of flow paths at a location on the facing wall portion side.

8. A Continuous Positive Airway Pressure (CPAP) device for sending air suctioned into the CPAP device to an airway of a user, the CPAP device comprising:
an air blower; and
a housing in which an air blower chamber is provided to accommodate the air blower, wherein the air blower includes an impeller rotatable about a rotation axis, a drive unit that drives to rotate the impeller, and a casing surrounding the impeller, the casing is provided with a suction port for suctioning air inside the air blower chamber into the casing, and a discharge port for discharging the air inside the casing to outside of the casing, the suction port is located at a top plate portion overlapping with the rotation axis, the top plate portion being one of a pair of wall portions of the casing, the pair of wall portions sandwiching the impeller in a direction in which the rotation axis extends, wall portions defining the air blower chamber include a wall portion that is located at a portion not overlapping with the top plate portion when seen along the direction in which the rotation axis extends and that is provided with an introduction port for introducing air outside the housing into the air blower chamber, the air blower chamber includes a facing wall portion facing the top plate portion with a distance between the facing wall portion and the top plate portion, in a space between the facing wall portion and the top plate portion, a flow adjustment portion that partitions at least a portion of the space into a plurality of flow paths arranged side by side around the rotation axis is provided, an outer end portion and an inner end portion of each of the plurality of flow paths in a direction orthogonal to the rotation axis include respectively a first open end and a second open end, the first open end and the second open end being open along the direction orthogonal to the rotation axis, the flow adjustment portion is provided on the facing wall portion to protrude toward the top plate portion, and the flow adjustment portion is located to be separated from the top plate portion.

9. The CPAP device according to claim 8, wherein an opening area of a first open end of a flow path of the plurality of flow paths on the introduction port side when seen from the suction port is smaller than an opening area of a first open end of another flow path of the plurality of flow paths on a side opposite to the introduction port side when seen from the suction port.

10. The CPAP device according to claim 9, wherein a first open end provided in the flow path of the plurality of flow paths at a shorter distance from the introduction port has a smaller opening area than the first open end of the other flow path.

11. The CPAP device according to claim 8, wherein the flow adjustment portion includes a plurality of flow adjustment plates that extend radially with respect to the rotation axis.

12. The CPAP device according to claim 11, wherein an inner end portion of each of the plurality of flow adjustment plates reaches an edge of the suction port.

13. The CPAP device according to claim 11, wherein
the plurality of flow adjustment plates include main flow adjustment plates each having a relatively long length and additional flow adjustment plates each having a relatively short length, and
one or a plurality of the additional flow adjustment plates are disposed between adjacent main flow adjustment plates.

14. The CPAP device according to claim 11, wherein the flow adjustment portion further includes an auxiliary flow adjustment plate in a form of a plate, the auxiliary flow adjustment plate being located on the facing wall portion side of each of the plurality of flow adjustment plates, the auxiliary flow adjustment plate closing each of the plurality of flow paths at a location on the facing wall portion side.

* * * * *